United States Patent
Danon et al.

(10) Patent No.: US 12,343,371 B2
(45) Date of Patent: *Jul. 1, 2025

(54) METHOD FOR SUPPRESSING OR ALLEVIATING PRIMARY OR SECONDARY PROGRESSIVE MULTIPLE SCLEROSIS (PPMS OR SPMS) USING A SUSTAINED RELEASE DEPOT FORMULATION COMPRISING GLATIRAMER ACETATE

(71) Applicant: MAPI PHARMA LTD., Ness Ziona (IL)

(72) Inventors: Uri Danon, Tel Aviv (IL); Nadav Bleich Kimelman, Tel Aviv (IL); Laura Popper, Tel Aviv (IL); Ehud Marom, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/495,458

(22) Filed: Oct. 6, 2021

(65) Prior Publication Data

US 2022/0023377 A1 Jan. 27, 2022

Related U.S. Application Data

(63) Continuation of application No. 16/497,120, filed as application No. PCT/IL2018/050340 on Mar. 25, 2018, now Pat. No. 11,167,003.

(60) Provisional application No. 62/476,794, filed on Mar. 26, 2017.

(51) Int. Cl.
| | |
|---|---|
| *A61K 38/00* | (2006.01) |
| *A61K 9/00* | (2006.01) |
| *A61K 38/02* | (2006.01) |
| *A61K 47/34* | (2017.01) |
| *A61P 25/00* | (2006.01) |
| *A61P 25/28* | (2006.01) |
| *A61K 38/10* | (2006.01) |
| *A61K 38/16* | (2006.01) |
| *A61K 39/00* | (2006.01) |
| *C07K 14/47* | (2006.01) |

(52) U.S. Cl.
CPC ............ *A61K 38/02* (2013.01); *A61K 9/0024* (2013.01); *A61K 47/34* (2013.01); *A61P 25/00* (2018.01); *A61P 25/28* (2018.01); *A61K 38/10* (2013.01); *A61K 38/16* (2013.01); *A61K 39/0008* (2013.01); *C07K 14/4713* (2013.01); *G01N 2800/285* (2013.01)

(58) Field of Classification Search
CPC .......... A61P 25/00; A61P 25/28; A61P 21/02; A61K 38/00; A61K 38/1825; A61K 38/08; A61K 38/16; A23P 10/30
See application file for complete search history.

(56) References Cited

U.S. PATENT DOCUMENTS

| | | |
|---|---|---|
| 3,536,809 A | 10/1970 | Norman |
| 3,598,123 A | 8/1971 | Zaffaroni |
| 3,773,919 A | 11/1973 | Boswell |
| 3,845,770 A | 11/1974 | Theeuwes |
| 3,849,550 A | 11/1974 | Teitelbaum |
| 3,916,899 A | 11/1975 | Theeuwes |
| 4,008,719 A | 2/1977 | Theeuwes |
| 4,822,340 A | 4/1989 | Kamstra |
| 5,059,595 A | 10/1991 | Le Grazie |
| 5,073,543 A | 12/1991 | Marshall |
| 5,120,548 A | 6/1992 | Mcclelland |
| 5,354,556 A | 10/1994 | Sparks |
| 5,578,442 A | 11/1996 | Desai |
| 5,591,767 A | 1/1997 | Mohr |
| 5,639,476 A | 6/1997 | Oshlack |
| 5,643,605 A | 7/1997 | Cleland |
| 5,674,533 A | 10/1997 | Santus |
| 5,733,559 A | 3/1998 | Citernesi |
| 5,792,477 A | 8/1998 | Rickey |
| 5,800,808 A | 9/1998 | Konfino |
| 5,858,964 A | 1/1999 | Aharoni |
| 5,945,126 A | 8/1999 | Thanoo et al. |
| 5,981,589 A | 11/1999 | Konfino |
| 6,048,898 A | 4/2000 | Konfino |
| 6,054,430 A | 4/2000 | Eliezer |
| 6,214,791 B1 | 4/2001 | Arnon |
| 6,309,669 B1 | 10/2001 | Setterstrom |
| 6,342,476 B1 | 1/2002 | Konfino |
| 6,362,161 B1 | 3/2002 | Konfino |
| 6,448,225 B2 | 9/2002 | O'Connor |

(Continued)

FOREIGN PATENT DOCUMENTS

| | | |
|---|---|---|
| AU | 2013203367 B2 | 6/2015 |
| CA | 2020477 C | 11/2000 |

(Continued)

OTHER PUBLICATIONS

Tselis et al., Neuropsych. Dis. Treat. 2007; 3:259-267.*

(Continued)

*Primary Examiner* — Chang-Yu Wang
(74) *Attorney, Agent, or Firm* — ROTHWELL, FIGG, ERNST AND MANBECK, P.C.

(57) ABSTRACT

The present invention provides methods for treating or ameliorating primary progressive multiple sclerosis (PPMS) or secondary progressive multiple sclerosis (SPMS) and related symptoms by administering or implanting a depot formulation comprising glatiramer salts, such as glatiramer acetate (GA).

17 Claims, 2 Drawing Sheets

(56) References Cited

U.S. PATENT DOCUMENTS

| | | |
|---|---|---|
| 6,454,746 B1 | 9/2002 | Bydlon |
| 6,506,410 B1 | 1/2003 | Park |
| 6,514,938 B1 | 2/2003 | Gad |
| 6,596,316 B2 | 7/2003 | Lyons |
| 6,620,847 B2 | 9/2003 | Konfino |
| 6,800,285 B2 | 10/2004 | Rodriguez |
| 6,800,287 B2 | 10/2004 | Gad |
| 6,835,711 B2 | 12/2004 | Eisenbach-Schwartz |
| 6,844,314 B2 | 1/2005 | Eisenbach-Schwartz |
| 6,861,064 B1 | 3/2005 | Laakso |
| 6,939,539 B2 | 9/2005 | Konfino |
| 7,022,663 B2 | 4/2006 | Gilbert |
| 7,033,582 B2 | 4/2006 | Yong |
| 7,074,580 B2 | 7/2006 | Gad |
| 7,163,802 B2 | 1/2007 | Gad |
| 7,195,778 B2 | 3/2007 | Fleshner-Barak |
| 7,199,098 B2 | 4/2007 | Konfino |
| 7,230,085 B2 | 6/2007 | Griffiths |
| 7,279,172 B2 | 10/2007 | Aharoni |
| 7,342,033 B2 | 3/2008 | Polman |
| 7,351,686 B2 | 4/2008 | Eisenbach-Schwartz |
| 7,381,790 B2 | 6/2008 | Strominger |
| 7,425,332 B2 | 9/2008 | Sela |
| 7,429,374 B2 | 9/2008 | Klinger |
| 7,495,072 B2 | 2/2009 | Dolitzky |
| 7,560,100 B2 | 7/2009 | Pinchasi |
| 7,576,051 B2 | 8/2009 | Kurokawa |
| 7,615,359 B2 | 11/2009 | Gad |
| 7,625,861 B2 | 12/2009 | Konfino |
| 7,635,695 B2 | 12/2009 | Burkitt |
| 7,655,221 B2 | 2/2010 | Rasmussen |
| 7,834,039 B2 | 11/2010 | Hobson |
| 7,855,176 B1 | 12/2010 | Altman |
| 7,923,215 B2 | 4/2011 | Klinger |
| 7,928,131 B2 | 4/2011 | Buzard |
| 7,968,511 B2 | 6/2011 | Vollmer |
| 8,008,258 B2 | 8/2011 | Aharoni |
| 8,138,201 B2 | 3/2012 | Kalafer |
| 8,232,250 B2 | 7/2012 | Klinger |
| 8,236,778 B2 | 8/2012 | Avila |
| 8,367,605 B2 | 2/2013 | Konfino |
| 8,377,885 B2 | 2/2013 | Marom |
| 8,389,228 B2 | 3/2013 | Klinger |
| 8,389,479 B2 | 3/2013 | Gelder |
| 8,394,763 B2 | 3/2013 | Forte |
| 8,399,211 B2 | 3/2013 | Gad |
| 8,399,413 B2 | 3/2013 | Klinger |
| 8,410,115 B2 | 4/2013 | Lieberburg |
| 8,440,622 B2 | 5/2013 | Stossel |
| 8,709,433 B2 | 4/2014 | Kasper |
| 8,759,302 B2 | 6/2014 | Dhib-Jalbut |
| 8,796,226 B2 | 8/2014 | Marom |
| 8,815,511 B2 | 8/2014 | Tchelet |
| 8,828,668 B2 | 9/2014 | Axtell |
| 8,920,373 B2 | 12/2014 | Altman |
| 8,969,302 B2 | 3/2015 | Klinger |
| 9,018,170 B2 | 4/2015 | Altman |
| 9,109,006 B2 | 8/2015 | Srinivasan |
| 9,114,136 B2 | 8/2015 | Kalafer |
| 9,155,775 B1 | 10/2015 | Cohen |
| 9,155,776 B2 | 10/2015 | Klinger |
| 9,200,114 B2 | 12/2015 | Marom |
| 9,402,874 B2 | 8/2016 | Klinger |
| 9,452,175 B2 | 9/2016 | Voskuhl |
| 9,702,007 B2 | 7/2017 | Tchelet |
| 10,493,122 B2* | 12/2019 | Sela ............... A61K 38/03 |
| 11,167,003 B2* | 11/2021 | Danon ............ A61P 25/00 |
| 11,413,311 B2* | 8/2022 | Marom ........... A61K 38/02 |
| 11,471,421 B2* | 10/2022 | Bleich Kimelman ............... C07K 14/001 |
| 2001/0007758 A1 | 7/2001 | Weiner |
| 2002/0037848 A1 | 3/2002 | Eisenbach-Schwartz |
| 2002/0077278 A1 | 6/2002 | Yong |
| 2002/0137681 A1 | 9/2002 | Steinman |
| 2003/0092059 A1 | 5/2003 | Salfeld |
| 2003/0104048 A1 | 6/2003 | Patel |
| 2003/0144286 A1 | 7/2003 | Frenkel |
| 2004/0038887 A1 | 2/2004 | Strominger |
| 2004/0106554 A1 | 6/2004 | Konfino |
| 2005/0014694 A1 | 1/2005 | Yong |
| 2005/0019322 A1 | 1/2005 | Rodriguez |
| 2005/0170004 A1 | 8/2005 | Rosenberger |
| 2005/0170005 A1 | 8/2005 | Rashba-Step |
| 2005/0171286 A1 | 8/2005 | Konfino |
| 2005/0277885 A1 | 12/2005 | Scherer |
| 2006/0154862 A1 | 7/2006 | Ray |
| 2006/0172942 A1 | 8/2006 | Dolitzky |
| 2006/0189527 A1 | 8/2006 | Rasmussen |
| 2006/0194725 A1 | 8/2006 | Rasmussen |
| 2006/0240463 A1 | 10/2006 | Lancet |
| 2006/0264354 A1 | 11/2006 | Aharoni |
| 2006/0276390 A1 | 12/2006 | Aharoni |
| 2007/0021324 A1 | 1/2007 | Dolitzky |
| 2007/0021341 A1 | 1/2007 | Sela |
| 2007/0037740 A1 | 2/2007 | Pinchasi |
| 2007/0048794 A1 | 3/2007 | Gad |
| 2007/0054857 A1 | 3/2007 | Pinchasi |
| 2007/0059798 A1 | 3/2007 | Gad |
| 2007/0081976 A1 | 4/2007 | Cohen |
| 2007/0135466 A1 | 6/2007 | Ledeboer |
| 2007/0161566 A1 | 7/2007 | Pinchasi |
| 2007/0173442 A1 | 7/2007 | Vollmer |
| 2007/0244056 A1 | 10/2007 | Hayardeny |
| 2007/0248569 A1 | 10/2007 | Eisenbach-Schwartz |
| 2008/0063687 A1 | 3/2008 | Chou |
| 2008/0085269 A1 | 4/2008 | Eisenbach-Schwartz |
| 2008/0118553 A1 | 5/2008 | Frenkel |
| 2008/0194462 A1 | 8/2008 | Wucherpfennig |
| 2008/0207526 A1 | 8/2008 | Strominger |
| 2008/0248122 A1 | 10/2008 | Rashba-Step |
| 2008/0261894 A1 | 10/2008 | Kreitman |
| 2008/0279819 A1 | 11/2008 | Went |
| 2009/0010885 A1 | 1/2009 | Vandenbark |
| 2009/0048181 A1 | 2/2009 | Schipper |
| 2009/0053253 A1 | 2/2009 | Klinger |
| 2009/0060873 A1 | 3/2009 | Sporn |
| 2009/0118298 A1 | 5/2009 | George |
| 2009/0130121 A1 | 5/2009 | Arnon |
| 2009/0149541 A1 | 6/2009 | Stark |
| 2009/0191173 A1 | 7/2009 | Eisenbach-Schwartz |
| 2009/0202527 A1 | 8/2009 | Panzara |
| 2009/0237078 A1 | 9/2009 | Shriver |
| 2010/0135953 A1 | 6/2010 | Eisenbach-Schwartz |
| 2010/0160894 A1 | 6/2010 | Julian |
| 2010/0167983 A1 | 7/2010 | Kreitman |
| 2010/0210817 A1 | 8/2010 | Gad |
| 2010/0226963 A1 | 9/2010 | Cooper |
| 2010/0285600 A1 | 11/2010 | Lancet |
| 2010/0298227 A1 | 11/2010 | Aharoni |
| 2010/0305023 A1 | 12/2010 | Stark |
| 2011/0046065 A1 | 2/2011 | Klinger |
| 2011/0060279 A1 | 3/2011 | Altman |
| 2011/0066112 A1 | 3/2011 | Altman |
| 2011/0195049 A1 | 8/2011 | Deftereos |
| 2011/0268699 A1 | 11/2011 | Deftereos |
| 2012/0027718 A1 | 2/2012 | Kreitman |
| 2012/0164229 A1 | 6/2012 | Marom |
| 2012/0199516 A1 | 8/2012 | Frohna |
| 2012/0269762 A1 | 10/2012 | Pickering |
| 2012/0276048 A1 | 11/2012 | Panzara |
| 2012/0309671 A1 | 12/2012 | Klinger |
| 2013/0165387 A1 | 6/2013 | Klinger |
| 2013/0309199 A1 | 11/2013 | Tegeder |
| 2013/0330277 A1 | 12/2013 | Blight |
| 2014/0056848 A1 | 2/2014 | Mak |
| 2014/0107208 A1 | 4/2014 | Comabella |
| 2014/0135254 A1 | 5/2014 | Fetzer |
| 2014/0193827 A1 | 7/2014 | Schwartz |
| 2014/0235670 A1 | 8/2014 | Tarcic et al. |
| 2014/0255346 A1 | 9/2014 | Kuerten |
| 2014/0271532 A1 | 9/2014 | Kreitman |
| 2014/0271630 A1 | 9/2014 | Vollmer |
| 2014/0294899 A1 | 10/2014 | Kasper |
| 2014/0322158 A1 | 10/2014 | Dhib-Jalbut |

(56) References Cited

U.S. PATENT DOCUMENTS

| | | |
|---|---|---|
| 2014/0348861 A1 | 11/2014 | Surolia |
| 2015/0044168 A1 | 2/2015 | Herbst |
| 2015/0045306 A1 | 2/2015 | Tchelet |
| 2015/0164977 A1 | 6/2015 | Klinger |
| 2015/0238602 A1 | 8/2015 | Cadavid |
| 2015/0359761 A1 | 12/2015 | Blitzer |
| 2016/0040236 A1 | 2/2016 | Hosur |
| 2016/0045570 A1 | 2/2016 | Bushnell |
| 2016/0213633 A1 | 7/2016 | Ladkani |
| 2016/0250172 A1 | 9/2016 | Goelz |
| 2016/0250251 A1 | 9/2016 | Klinger |
| 2016/0347816 A1 | 12/2016 | Toporik |
| 2017/0022276 A1 | 1/2017 | Lieberburg |
| 2017/0029522 A1 | 2/2017 | Smith |
| 2020/0147141 A1 | 5/2020 | Marom |

FOREIGN PATENT DOCUMENTS

| | | |
|---|---|---|
| CN | 1398584 A | 2/2003 |
| CN | 103169670 A | 6/2013 |
| CN | 104349792 A | 2/2015 |
| EP | 1528922 B1 | 3/2006 |
| EP | 1261361 B1 | 6/2006 |
| EP | 0975351 B1 | 3/2007 |
| EP | 1799703 B1 | 1/2010 |
| EP | 2275086 B1 | 3/2012 |
| EP | 2500072 A1 | 9/2012 |
| EP | 2405749 B1 | 5/2013 |
| EP | 2424513 B1 | 5/2015 |
| EP | 1797109 B1 | 2/2016 |
| EP | 2139467 B1 | 9/2016 |
| EP | 2949335 B1 | 1/2017 |
| EP | 3130349 A1 | 2/2017 |
| EP | 3409286 * | 12/2018 |
| EP | 3409286 A1 | 12/2018 |
| JP | H01121222 A | 5/1989 |
| JP | 2002-500631 A | 1/2002 |
| JP | 2007-500693 A | 1/2007 |
| JP | 2007-509981 A | 4/2007 |
| JP | 2007-517902 A | 7/2007 |
| JP | 2007-531701 A | 11/2007 |
| JP | 2009-515999 A | 4/2009 |
| JP | 2016-510343 A | 4/2016 |
| WO | 9501096 A1 | 1/1995 |
| WO | 9531990 A1 | 11/1995 |
| WO | 97026869 A1 | 7/1997 |
| WO | 98030227 A1 | 7/1998 |
| WO | 00005249 A2 | 2/2000 |
| WO | 0005250 A1 | 2/2000 |
| WO | 00018794 A1 | 4/2000 |
| WO | 00020010 A1 | 4/2000 |
| WO | 0027417 A1 | 5/2000 |
| WO | 0152878 A2 | 7/2001 |
| WO | 01060392 A1 | 8/2001 |
| WO | 0193893 A2 | 12/2001 |
| WO | 01093828 A1 | 12/2001 |
| WO | 01097846 A1 | 12/2001 |
| WO | 03048735 A2 | 6/2003 |
| WO | 2004043995 A2 | 5/2004 |
| WO | 2004064717 A2 | 8/2004 |
| WO | 2004091573 A1 | 10/2004 |
| WO | 2004103297 A2 | 12/2004 |
| WO | 2005009333 A2 | 2/2005 |
| WO | 2005035088 A2 | 4/2005 |
| WO | 2005041933 A1 | 5/2005 |
| WO | 2005070332 A1 | 8/2005 |
| WO | 2005084377 A2 | 9/2005 |
| WO | 2005085323 A2 | 9/2005 |
| WO | 2005120542 A2 | 12/2005 |
| WO | 2006029036 A2 | 3/2006 |
| WO | 2006029393 A2 | 3/2006 |
| WO | 2006029411 A2 | 3/2006 |
| WO | 2006050122 A1 | 5/2006 |
| WO | 2006057003 A2 | 6/2006 |
| WO | 2006083608 A1 | 8/2006 |
| WO | 2006089164 A1 | 8/2006 |
| WO | 2006116602 A2 | 11/2006 |
| WO | 2007021970 A2 | 2/2007 |
| WO | 2007022254 A2 | 2/2007 |
| WO | 2007030573 A2 | 3/2007 |
| WO | 2007059342 A2 | 5/2007 |
| WO | 2007081975 A2 | 7/2007 |
| WO | 2008006026 A1 | 1/2008 |
| WO | 2008075365 A1 | 6/2008 |
| WO | 2009040814 A1 | 4/2009 |
| WO | 2009063459 A2 | 5/2009 |
| WO | 2009070298 A1 | 6/2009 |
| WO | 2010011879 A2 | 1/2010 |
| WO | 2010024908 A1 | 3/2010 |
| WO | 2011008274 A2 | 1/2011 |
| WO | 2011022063 A1 | 2/2011 |
| WO | 2011080733 A1 | 7/2011 |
| WO | 2012051106 A1 | 4/2012 |
| WO | 2012143924 A1 | 10/2012 |
| WO | 2013055683 A1 | 4/2013 |
| WO | 2013171345 A1 | 11/2013 |
| WO | 2014058976 A2 | 4/2014 |
| WO | 2014107533 A2 | 7/2014 |
| WO | 2014165280 A1 | 10/2014 |
| WO | 2015037000 A1 | 3/2015 |
| WO | 2015037005 A1 | 3/2015 |
| WO | 2015168000 A1 | 11/2015 |
| WO | 2016036719 A1 | 3/2016 |
| WO | 2016036721 A1 | 3/2016 |
| WO | 2016040861 A1 | 3/2016 |
| WO | 2016064997 A1 | 4/2016 |
| WO | 2016112270 A1 | 7/2016 |
| WO | 2016160830 A1 | 10/2016 |
| WO | 2016160832 A1 | 10/2016 |
| WO | 2018002930 A1 | 1/2018 |
| WO | 2018042415 A1 | 3/2018 |
| WO | 2018042423 A1 | 3/2018 |
| WO | WO2018042423 * | 3/2018 |

OTHER PUBLICATIONS

Milo et al., Autoimmunity Rev. 2014; 13:518-524.*
INFORMS (clinical trials: NCT00731692) retrieved from the NIH clinical trial website: clinicaltrials.gov/ct2/show/NCT00731692 on Nov. 21, 2020.*
Polman et al., Ann Neurol. 2005; 58:840-846.*
Wolinsky et al. J. Neurol. Scie. 2009; 286:92-98.*
Polman et al., Ann Neurol. 2011; 69:292-302.*
"Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL: www.tevapharm.com/Media/News/Pages/2012/1743500.aspx?year=2012&page>.
"Design and development of sustained release or controlled release agents", chief edited by Yaodong Yan, Chinese medical science and technology press, First edition on May 2006; pp. 10-29. Translation of relevant portions.
1996 FDA Meeting Agenda minutes from the Peripheral and Central Nervous System Drug Advisory Committee (dated Sep. 19, 1996) (Exhibit A to Exhibit 1019).
3-Times-A-Week Copaxone® 40 Mg, Teva. Retrieved from: https://www.copaxone.com/about-copaxone/copaxone-40-mg on Mar. 10, 2016.
A Multinational, Multicenter, Randomized, Double-Blind, Placebo-Controlled, Parallel-Group Study to Assess the Efficacy, Tolerability and Safety of 40 mg Glatiramer Acetate Injection in Subjects with Amyotrophic Lateral Sclerosis. Protocol ALS-GA-201 (GoALS); Eudract No. 2006-001688-49. Summary of Clinical Trial Results; Jul. 2008. Publication date: Feb. 9, 2018 Retrieved from: https://www.clinicaltrialsregister.eu/ctr-search/trial/2006-001688-49/GB; 62 pages.
A Pilot, Multi-Center, Open-Label, One-Group Study to Explore the Efficacy, Tolerability and Safety of an Oral Once-daily 600 mg Dose of Glatiramer Acetate (GA) in Subjects with Relapsing Remitting (R-R) Multiple Sclerosis (MS). Protocol GA/7026; EudraCT No.

(56) References Cited

OTHER PUBLICATIONS 2004-000463-94. Study Conducted (Sep. 2004-Mar. 2006). Summary of Results; Feb. 2007. Publication date: Jan. 4, 2017. Retrieved from: https://www.clinicaltrialsregister.eu/ctr-search/trial/2004-000463-94/results; 25 pages.
A Study to Test the Effectiveness and Safety of a New Higher 40mg Dose of Copaxone® Compared to Copaxone® 20mg, the Currently Approved Dose [online]. ClinicalTrials.gov, 1993 [retrieved on Feb. 13, 2015]. Retrieved from the Internet: <URL: clinicaltrials.gov/show/NCT00202982>; 6 pages.
A to Z of MS Alemtuzumab (Lemtrada), Multiple Sclerosis Trust, retrieved on Jun. 2, 2015. http://bit.ly/1YnIfHQ.
Abramsky et al., (1977) Effect of a synthetic polypeptide (COP 1) on patients with multiple sclerosis and with acute disseminated encephalomeylitis. Preliminary report. J Neurol Sci 31(3): 433-438.
Aharoni (2013) The mechanism of action of glatiramer acetate in multiple sclerosis and beyond. Autoimmun Rev 12(5): 543-553.
Aharoni et al., (1997) Copolymer 1 induces T cells of the T helper type 2 that crossreact with myelin basic protein and suppress experimental autoimmune encephalomyelitis. Proc Natl Acad Sci U S A 94(20): 10821-10826.
Aharoni et al., (2000) Specific Th2 cells accumulate in the central nervous system of mice protected against experimental autoimmune encephalomyelitis by copolymer 1. Proc Natl Acad Sci U S A 97(21): 11472-11477.
Aharoni et al., (2003) Glatiramer acetate-specific T cells in the brain express T helper 2/3 cytokines and brain-derived neurotrophic factor in situ. Proc Natl Acad Sci U S A 100(24): 14157-14162.
Aharoni et al., (2005) Therapeutic effect of the immunomodulator glatiramer acetate on trinitrobenzene sulfonic acid-induced experimental colitis. Inflamm Bowel Dis 11(2): 106-115.
Alison Palkhivala; Doubling the Dose of Glatiramer Acetate Does Not Increase Efficacy. Medscape Medical News (Sep. 22, 2008). Retrieved on Jan. 6, 2015. 2 pages.
All About MS. Posted by: Thixia | Apr. 11, 2008. Retrieved from: https://scamparoo.wordpress.com/2008/04/11/ms-therapies-copaxone/ (dated Apr. 11, 2008 (accessed Feb. 5, 2015)).
Ampyra Prescribing Information, Acorda Therapeutics (Dec. 2014).
Anand Geeta; Through Charities, Drug Makers Help People—and Themselves, Wall St. J. (Dec. 1, 2005), retrieved on Mar. 8, 2016 http://www.wsj.com/articles/SB113339802749110822.
Anderson and Shive (1997) Biodegradation and biocompatibility of PLA and PLGA microspheres. Advanced Drug Delivery Reviews 28: 5-24.
Anderson et al., (1992) Revised estimate of the prevalence of multiple sclerosis in the United States. Ann Neurol 31(3): 333-336.
Anderson et al., (2010) Injection pain decreases with new 0.5 mL formulation of glatiramer acetate. International Journal of MS Care 12(supp 1): 54. Abstracts from the 24th Annual Meeting of the Consortium of Multiple SclerosiCenters; Multiple Sclerosis: Sustaining Care, Seeking a Cure, Jun. 2-5, 2010; San Antonio, TX, USA.
Anderson et al., (2010) Tolerability and safety of novel half milliliter formulation of glatiramer acetate for subcutaneous injection: an open-label, multicenter, randomized comparative study. J Neurol 257(11): 1917-1923.
Arnon (1996) The development of Cop 1 (Copaxone®), an innovative drug for the treatment of multiple sclerosis: personal reflections. Immunol Lett 50(1-2): 1-15.
Arnon and Aharoni (2004) Mechanism of action of glatiramer acetate in multiple sclerosis and its potential for the development of new applications. Proc Natl Acad Sci U S A 101 Suppl 2(Suppl 2): 14593-14598.
Arnon and Aharoni (2007) Neurogenesis and neuroprotection in the CNS—fundamental elements in the effect of Glatiramer acetate on treatment of autoimmune neurological disorders. Mol Neurobiol 36(3): 245-253.
Avonex® Product Label (2006).

Bains et al., (2010) Glatiramer acetate: successful desensitization for treatment of multiple sclerosis. Ann Allergy Asthma Immunol 104(4): 321-325.
Bakshi et al., (2005) Imaging of multiple sclerosis: role in neurotherapeutics. NeuroRx 2(2): 277-303.
Bartus et al., (1998) Sustained delivery of proteins for novel therapeutic products. Science 281(5380): 1161-1162.
Beer et al., (2011) The prevalence of injection-site reactions with disease-modifying therapies and their effect on adherence in patients with multiple sclerosis: an observational study. BMC Neurol 11: 144.
Benet LZ et al., Pharmacokinetics: The Dynamics of Drug Absorption, Distribution, and Elimination. In: Goodman & Gilman's The Pharmacological Basis of Therapeutics, 9th edition. McGraw-Hill, 1996. pp. 3-27.
Beringer P and Winter ME; Clinical Pharmacokinetics and Pharmacodynamics. In Remington: The Science and Practice of Pharmacy. Paul Beringer ed., 21st edition (2005). Lippincott Williams & Wilkins. pp. 1191-1205, 1197, 1201.
Bermel and Bakshi (2006) The measurement and clinical relevance of brain atrophy in multiple sclerosis. Lancet Neurol 5(2): 158-170.
Berndt et al., (1995) Information, marketing, and pricing in the U.S. antiulcer drug market. Am Econ Rev 85(2): 100-105.
Berndt et al., (2002) An analysis of the diffusion of new antidepressants: variety, quality, and marketing efforts. J Ment Health Policy Econ 5(1): 3-19.
Betaseron® U.S. Product Label (Oct. 2003).
Bjartmar and Fox (2002) Pathological mechanisms and disease progression of multiple sclerosis: therapeutic implications. Drugs Today (Barc) 38(1): 17-29.
Blanco et al., (2006) Effect of glatiramer acetate (Copaxone®) on the immunophenotypic and cytokine profile and BDNF production in multiple sclerosis: a longitudinal study. Neurosci Lett 406(3): 270-275.
Boissel and Nony (2002) Using pharmacokinetic-pharmacodynamic relationships to predict the effect of poor compliance. Clin Pharmacokinet 41(1): 1-6.
Bornstein et al., "Treatment of Multiple Sclerosis with Copolymer 1" in Treatment of Multiple Sclerosis: Trial Design, Results and Future Perspectives (Rudick R.A. & Good kin D. E., eds., Springer Lerlag, London, 1992) 173-198. Abstract.
Bornstein et al., "Clinical Trials of a Synthetic Polypeptide (Copolymer 1) for the treatment of Mutliple Sclerosis". In: Gonsett et al., Immunological and Clinical Aspects of Multiple Sclerosis (MTP Press, The Hague, 1984), pp. 144-150. Abstract.
Bornstein et al., (1980) Treatment of multiple sclerosis with a synthetic polypeptide: preliminary results. Trans Am Neurol Assoc 105: 348-350.
Bornstein et al., (1982) Multiple sclerosis: trial of a synthetic polypeptide. Ann Neurol 11(3): 317-319.
Bornstein et al., (1984) Clinical trials of copolymer I in multiple sclerosis. Ann N Y Acad Sci 436: 366-372.
Bornstein et al., (1987) A pilot trial of Cop 1 in exacerbating-remitting multiple sclerosis. N Engl J Med 317(7): 408-414.
Bornstein et al., (1988) Clinical experience with COP-1 in multiple sclerosis. Neurology 38(7 Suppl 2): 66-69. Abstract.
Bornstein et al., (1991) A placebo-controlled, double-blind, randomized, two-center, pilot trial of Cop 1 in chronic progressive multiple sclerosis. Neurology 41(4): 533-539.
Bornstein; Clinical Experience: hopeful prospects in multiple sclerosis:. Hospital Practice (Off. Ed.), 1992, vol. 27, No. 5, pp. L135-158, 141-142, 145-158. 1st page.
Brunkow et al., (2001) Disruption of a new forkhead/winged-helix protein, scurfin, results in the fatal lymphoproliferative disorder of the scurfy mouse. Nat Genet 27(1): 68-73.
Bala et al., (2004) PLGA nanoparticles in drug delivery: the state of the art. Critical Reviews™ in Therapeutic Drug Carrier Systems 21(5): 387-422.
Burger et al., (2009) Glatiramer acetate increases IL-1 receptor antagonist but decreases T cell-induced IL-1ß in human monocytes and multiple sclerosis. Proc Natl Acad Sci U S A 106(11): 4355-4359.

(56) References Cited

OTHER PUBLICATIONS

Caon et al., (2009) Randomized, Prospective, Rater-Blinded, Four Year Pilot Study to Compare the Effect of Daily Versus Every Other Day Glatiramer Acetate 20 mg Subcutaneous Injections in RRMS Neurology 72:11(3): A317.
Castells (2009) Rapid desensitization for hypersensitivity reactions to medications. Immunol Allergy Clin North Am 29 (3): 585-606.
Chabot et al., (2002) Cytokine production in T lymphocyte-microglia interaction is attenuated by glatiramer acetate: a mechanism for therapeutic efficacy in multiple sclerosis. Mult Scler 8(4): 299-306.
Chantelau et al., (1991) What makes insulin injections painful? BMJ 303(6793): 26-27.
Chapter 8: Drug elimination and pharmacokinetics. pp. 106-119. H.P. Pharmacology (5th ed. 2005); edited by Rang HP, Dale MM, Ritter JM and Moore PK.
Chen et al., (1991) Mu receptor binding of some commonly used opioids and their metabolites. Life Sci 48(22): 2165-2171.
Chen et al., (2002) Sustained immunological effects of Glatiramer acetate in patients with multiple sclerosis treated for over 6 years. J Neurol Sci 201(1-2): 71-77.
Cohen et al., (2012) Alemtuzumab versus interferon beta 1a as first-line treatment for patients with relapsing-remitting multiple sclerosis: a randomised controlled phase 3 trial. Lancet 380(9856): 1819-1828.
Comi and Moiola (2002) Glatiramer acetate. Neurologia 17(5): 244-258.
Comi et al., (2001) European/Canadian multicenter, double-blind, randomized, placebo-controlled study of the effects of glatiramer acetate on magnetic resonance imaging—measured disease activity and burden in patients with relapsing multiple sclerosis. European/Canadian Glatiramer Acetate Study Group. Ann Neurol 49(3): 290-297.
Comi et al., (2008) Results from a phase III, 1-year, Randomized, Double-blind, Parallel-Group, Dose-Comparison Study with Glatiramer Acetate in Relapsing-Remitting Multiple Sclerosis. Mult Scler 14: S299-S301.
Comi et al., (2009) Effect of glatiramer acetate on conversion to clinically definite multiple sclerosis in patients with clinically isolated syndrome (PreCISe study): a randomised, double-blind, placebo-controlled trial. Lancet 374(9700): 1503-1511.
Comi G. "Treatment with glatiramer acetate delays conversion to clinically definite multiple sclerosis (CDMS) in patients with clinically isolated syndromes (CIS)". Program and abstracts of the American Academy of Neurology 60th Annual Meeting; Apr. 12-19, 2008; Chicago, Illinois. LBS.003.
Conner (2014) Glatiramer acetate and therapeutic peptide vaccines for multiple sclerosis. Journal of Autoimmunity and Cell Responses 1: Article 3; 11 pages.
Copaxone 20 mg/ml or Copaxone 40 mg/ml, NDA 020622/S-089 FDA Approved Labeling Text dated Jan. 28, 2014.
Copaxone 20 mg/ml, Solution for Injection, Pre-Filled Syringe, Summary of Product Characteristics updated on Apr. 17, 2009.
Copaxone Prescribing Information (Jan. 2014). 8 pages.
Copaxone, https://scamparoo.wordpress.com/2008/04/11/mstherapies-copaxone/ (dated Apr. 11, 2008 (accessed Feb. 5, 2015)).
Copaxone® U.S. Product Label (2001).
Copaxone® U.S. Product Label (Feb. 2009).
Copaxone®, Food and Drug Administration Approved Labeling, Jan. 2014, submitted as Exhibit 1057 in Inter Partes Review Case No. IPR2015-00643.
Copaxone®, Physicians' Desk Reference, 62nd ed. Montvale, NJ, Thomson Healthcare Inc., pp. 3231-3235 (2008).
Costello et al., (2008) Recognizing nonadherence in patients with multiple sclerosis and maintaining treatment adherence in the long term. Medscape J Med 10(9): 225.
David J and Stewart MB; Commercial Success: Economic Principles Applied to Patent Litigation. In: Economic Damages in Intellectual Property: A Hands-On Guide to Litigation. Edited by Slottje D. John Wiley & Sons, Inc. 2006. pp. 159-170.
De Stefano et al., (2009) The results of two multicenter, open-label studies assessing efficacy, tolerability and safety of protiramer, a high molecular weight synthetic copolymeric mixture, in patients with relapsing-remitting multiple sclerosis. Mult Scler 15(2): 238-243.
De Stefano et al., (2010) Assessing brain atrophy rates in a large population of untreated multiple sclerosis subtypes. Neurology 74(23): 1868-1876.
De Vijlder (2003) Primary congenital hypothyroidism: defects in iodine pathways. Eur J Endocrinol 149(4): 247-256.
Devonshire et al., (2006) The Global Adherence Project—A multicentre observational study on adherence to disease-modifying therapies in patients suffering from relapsing-remitting multiple sclerosis, Multiple Sclerosis 12: S1 (P316).
Dhib-Jalbut (2002) Mechanisms of action of interferons and glatiramer acetate in multiple sclerosis. Neurology 58(8 Suppl 4): S3-S9.
Dhib-Jalbut (2003) Glatiramer acetate (Copaxone) therapy for multiple sclerosis. Pharmacol Ther 98(2): 245-255. Abstract.
DiPiro et al., Introduction to pharmacokinetics and pharmacodynamics. In: Concepts in Clinical Pharmacodynamics (5th ed. 2010). pp. 1-17.
Duda et al., (2000) Glatiramer acetate (Copaxone®) induces degenerate, Th2-polarized immune responses in patients with multiple sclerosis. J Clin Invest 105(7): 967-976.
Edgar et al., (2004) Lipoatrophy in patients with multiple sclerosis on glatiramer acetate. Can J Neurol Sci 31(1): 58-63.
Efimova et al., (2005) Changes in the secondary structure of proteins labeled with 125I: CD spectroscopy and enzymatic activity studies. Journal of Radioanalytical and Nuclear Chemistry 264(1): 91-96.
Extavia® Product Label (2009). Prescribing information.
Extavia®, Abbreviated Drug Monograph: Interferon beta 1b (Extavia®), Sep. 2010, submitted as Exhibit 1053 in Inter Partes Review Case Nos. IPR2015-00643, IPR2015-00644 and IPR2015-00830.
Farina et al., (2001) Treatment of multiple sclerosis with Copaxone (COP): Elispot assay detects COP-induced interleukin-4 and interferon-gamma response in blood cells. Brain 124(Pt 4): 705-719.
FDA approves new MS treatment regimen developed at Wayne State University by Dr. Omar Khan, Division of Research—Research@Wayne, https://research.wayne.edu/rwnews/article.php?id=1319 (Posted on: Thursday, Jan. 30, 2014; last visited Mar. 8, 2016).
FDA Guidance for Industry—Population Pharmacokinetics (1999). 35 pages.
FDA Guidance for Industry—Statistical Approaches to Establishing Bioequivalence (2001). 48 pages.
FDA, Guideline for Industry: Dose-Response Information to Support Drug Registration (1994).
Figure: Perception of 3-times-a-week Copaxone 40mg compared to Daily Copaxone 20mg. 2015.
Figure: Perceptions of Copaxone® 40mg compared to Daily Generic GA. 2015.
Figure: Perceptions of Copaxone® 40mg vs. 20mg. 2015.
Figure: Rationale for Discussing 20mg and 40mg for First Line Patients. 2015.
Figure: Rationale for Requesting Copaxone. 2015.
Filippi et al., (2006) Effects of oral glatiramer acetate on clinical and MRI-monitored disease activity in patients with relapsing multiple sclerosis: a multicentre, double-blind, randomised, placebo-controlled study. Lancet Neurol, neurology.thelancet.com. Published online Jan. 20, 2006 DOI:10.1016/S1474-4422(06)70327-1. 8 pages.
Filippi et al., (2010) The contribution of MRI in assessing cognitive impairment in multiple sclerosis. Neurology 75(23): 2121-2128.
Fisher et al., (2008) Gray matter atrophy in multiple sclerosis: a longitudinal study. Ann Neurol 64(3): 255-265.
Kragt et al., (2006) How similar are commonly combined criteria for EDSS progression in multiple sclerosis? Mult Scler 12(6): 782-786.
Lambert and Laurent (2008) Intradermal vaccine delivery: will new delivery systems transform vaccine administration? Vaccine 26(26): 3197-3208.

(56) References Cited

OTHER PUBLICATIONS

Lando et al., (1979) Effect of cyclophosphamide on suppressor cell activity in mice unresponsive to EAE. J Immunol 123(5): 2156-2160.

LeBano Lauren (2012) Gray Matter Atrophy May Serve as an Effective Outcome measure for MS Clinical Trials. Neurology Reviews 20(2): 8. 5 pages.

Lisak RP and Kira J-I 'Chapter 100, Multiple Sclerosis'. In: International Neurology a Clinical Approach. Edited by: Lisak et al., pp. 366-374, Wiley-Blackwell.

Lobel et al., (1996) Copolymer-1. Drugs of the Future 21(2): 131-134.

Lublin et al., (2003) Effect of relapses on development of residual deficit in multiple sclerosis. Neurology 61(11): 1528-1532.

Luzzio C & Keegan BM Multiple Sclerosis Medication, Medscape Reference (Nov. 24, 2014), retrieved on May 28, 2015. http://emedicine.medscape.com/article/1146199-medication#1.

Manso and Sokol (2006) Life cycle management of ageing pharmaceutical assets. Pharmaceutical Law Insight 3(7): 16-19.

Marketing Materials, PRA, Multiple Sclerosis: Transform Your Clinical Trial with PRA (2012) (on file with author) (Peroutka Dep. Ex. 4).

McBride (2002) Nonadherence to immunomodulation in multiple sclerosis. Int'l J MS Care 4: 85. Presented at the Second International Multiple Sclerosis Week. Multiple Sclerosis: A World View. Hyatt Regency Chicago, Illinois, USA; Jun. 5-9, 2002.

McDonald et al., (2001) Recommended diagnostic criteria for multiple sclerosis: Guidelines from the international panel on the diagnosis of multiple sclerosis. Annals of Neurology 50(1): 121-127.

McEwan et al., (2010) Best Practices in Skin Care for the Multiple Sclerosis Patient Receiving Injectable Therapies. Int J MS Care 12(4): 177-189.

McKeage (2015) Glatiramer Acetate 40 mg/mL in Relapsing-Remitting Multiple Sclerosis: A Review. CNS Drugs; Published online: Apr. 24, 2015. 8 pages.

Medical News Today; Multiple Sclerosis—Teva Provides Update on FORTE Trial. Article Date: Jul. 8, 2008. Retrieved from://web.archive.org/web/20090103103610/http://www.medicalnewstoday.com/articles/114183.php; 3 pages.

Meibohm and Derendorf (1997) Basic concepts of pharmacokinetic/pharmacodynamic (PK/PD) modelling. Int J Clin Pharmacol Ther 35(10): 401-413.

Meiner Z et al., (1997) Copolymer 1 in relapsing-remitting multiple sclerosis: a multi-centre trial. In: Frontiers in Multiple Sclerosis: Clinical Research and Therapy. Edited by Abramsky O and Ovadia Hpp. 213-221.

Mendes and Sá (2011) Classical immunomodulatory therapy in multiple sclerosis: how it acts, how it works. Arq Neuropsiquiatr 69(3): 536-543.

Menge et al., (2008) Disease-modifying agents for multiple sclerosis: recent advances and future prospects. Drugs 68 (17): 2445-2468.

Miller (2004) The importance of early diagnosis of multiple sclerosis. J Manag Care Pharm 10(3 Suppl B): S4-S11.

Miller et al., (1998) Treatment of multiple sclerosis with copolymer-1 (Copaxone®): implicating mechanisms of Th1 to Th2/Th3 immune-deviation. J Neuroimmunol 92(1-2): 113-121.

Miller et al., (2005) Clinically isolated syndromes suggestive of multiple sclerosis, part I: natural history, pathogenesis, diagnosis, and prognosis. Lancet Neurol 4(5): 281-288. Abstract.

Miller et al., (2005) Clinically isolated syndromes suggestive of multiple sclerosis, part 2: non-conventional MRI, recovery processes, and management. Lancet Neurol 4(6): 341-348. Abstract.

Miller et al., (2007) Experimental autoimmune encephalomyelitis in the mouse. Current Protocols in Immunology 15.1.1-15.1.13.

Minneboo et al., (2008) Predicting short-term disability progression in early multiple sclerosis: added value of MRI parameters. J Neurol Neurosurg Psychiatry 79(8): 917-923.

MomentumMagazineOnline.com; 10 Disease-Modifying Treatments, Nov. 2013, available at http://bit.ly/1eVa0jT.

Monro (1993) The paradoxical lack of interspecies correlation between plasma concentrations and chemical carcinogenicity. Regul Toxicol Pharmacol 18(1): 115-135.

Neuhaus et al., (2000) Multiple sclerosis: comparison of copolymer-1-reactive T cell lines from treated and untreated subjects reveals cytokine shift from T helper 1 to T helper 2 cells. Proc Natl Acad Sci U S A 97(13): 7452-7457.

Neuhaus et al., (2001) Mechanisms of action of glatiramer acetate in multiple sclerosis. Neurology 56(6): 702-708.

Neuhaus et al., (2003) Immunomodulation in multiple sclerosis: from immunosuppression to neuroprotection. Trends Pharmacol Sci 24(3): 131-138. Abstract.

Neuhaus et al., (2007) Pharmacokinetics and pharmacodynamics of the interferon-betas, glatiramer acetate, and mitoxantrone in multiple sclerosis. J Neurol Sci 259(1-2): 27-37.

Noseworthy et al., (2000) Multiple sclerosis. N Engl J Med 343(13): 938-952.

O'Connor et al., (2009) 250 microg or 500 microg interferon beta-1b versus 20 mg glatiramer acetate in relapsing-remitting multiple sclerosis: a prospective, randomised, multicentre study. Lancet Neurol 8(10): 889-897 with errata.

Oksenberg et al., (1992) A single amino-acid difference confers major pharmacological variation between human and rodent 5-HT1B receptors. Nature 360(6400): 161-163.

O'Neill (1997) Secondary endpoints cannot be validly analyzed if the primary endpoint does not demonstrate clear statistical significance. Controlled Clinical Trials 18(6): 550-556.

Opinion, Endo Pharmaceuticals, Inc. v. Mylan Pharmaceuticals, Inc., No. 11-cv-00717, Document 226 (D. Del. Jan. 28, 2014) (Peroutka Dep. Ex. 6). 108 pages.

Orange Book: Approved Drug Products with Therapeutic Equivalence Evaluations. Retrieved from: http://www.accessdata.fda.gov/scripts/cder/ob/docs/patexclnew.cfm?Appl_No=020622&Product_No=003&table1=OB_Rx (accessed Feb. 5, 2015). 7 pages.

Orelli Brian; Momenta Slowed (Temporarily), The Motley Fool (Nov. 7, 2015), retrieved on Dec. 28, 2015. http://bit.ly/1YiNNmS.

Osborne (2009) Buzz around Campath proof-of-concept trial in MS. Nat Biotechnol 27(1): 6-8.

Paolillo et al., (2004) The relationship between inflammation and atrophy in clinically isolated syndromes suggestive of multiple sclerosis: a monthly MRI study after triple-dose gadolinium-DTPA. J Neurol 251(4): 432-439.

Pardo et al., (2007) Impact of an oral antihistamine on local injection site reactions with glatiramer acetate. Multiple Sclerosis 13: S134. Abstract P455.

Partidos et al., (2003) Immunity under the skin: potential application for topical delivery of vaccines. Vaccine 21(7-8): 776-780.

Paty (1994) The interferon-β1b clinical trial and its implications for other trials. Ann Neurol 36 Suppl: S113-S114.

Pelidou et al., (2008) Multiple sclerosis presented as clinically isolated syndrome: the need for early diagnosis and treatment. Ther Clin Risk Manag 4(3): 627-630.

Peroutka (1988) Antimigraine drug interactions with serotonin receptor subtypes in human brain. Ann Neurol 23(5): 500-504.

Pert and Snyder (1973) Properties of opiate-receptor binding in rat brain. Proc Natl Acad Sci U S A 70(8): 2243-2247.

Petty et al., (1994) The effect of systemically administered recombinant human nerve growth factor in healthy human subjects. Ann Neurol 36(2): 244-246.

Prescribing Information, EMD Serono, Rebif Prescribing Information (Sep. 2009).

Racke and Lovett-Racke (2011) Glatiramer acetate treatment of multiple sclerosis: an immunological perspective. J Immunol 186(4): 1887-1890.

Ramot et al., (2016) Biocompatibility and safety of PLA and its copolymers. Adv Drug Deliv Rev 107: 153-162.

Ravivarapu et al., "Biodegradable Polymeric Delivery Systems". In: Design of Controlled Release Drug Delivery Systems. Li X and Jasti BR (eds.). McGraw-Hill Chemical Engineering, 2006, pp. 271-303.

(56) References Cited

OTHER PUBLICATIONS

Reagan-Shaw et al., (2008) Dose translation from animal to human studies revisited. FASEB J 22(3): 659-661.
Rotstein et al., (2015) Evaluation of no evidence of disease activity in a 7-year longitudinal multiple sclerosis cohort. JAMA Neurol 72(2): 152-158.
Ruggieri et al., (2007) Glatiramer acetate in multiple sclerosis: a review. CNS Drug Rev 13(2): 178-191.
Sabatos-Peyton et al., (2010) Antigen-specific immunotherapy of autoimmune and allergic diseases. Curr Opin Immunol 22(5): 609-615.
Sayed et al., (2011) Cutting edge: mast cells regulate disease severity in a relapsing-remitting model of multiple sclerosis. J Immunol 186(6): 3294-3298.
Sela et al., (1990) Suppressive activity of Cop-1 in EAE and its Relevance to Multiple Sclerosis. Bull. Inst. Pasteur (Paris) 88: 303-314.
Shenoy et al., (2002) Poly(DL-lactide-co-glycolide) microporous microsphere-based depot formulation of a peptide-like antineoplastic agent. J Microencapsul 19(4): 523-535.
Sorensen et al., (1998) Intravenous immunoglobulin G reduces MRI activity in relapsing multiple sclerosis. Neurology 50(5): 1273-1281.
Stern et al., (2008) Amino acid copolymer-specific IL-10-secreting regulatory T cells that ameliorate autoimmune diseases in mice. Proc Natl Acad Sci USA 105(13): 5172-5176.
Tabansky et al., (2015) Advancing drug delivery systems for the treatment of multiple sclerosis. Immunol Res 63(1-3): 58-69.
Teitelbaum et al., (1971) Suppression of experimental allergic encephalomyelitis by a synthetic polypeptide. Eur J Immunol 1(4): 242-248.
Teitelbaum et al., (1973) Suppression by several synthetic polypeptides of experimental allergic encephalomyelitis induced in guinea pigs and rabbits with bovine and human basic encephalitogen. Eur J Immunol 3(5): 273-279.
Teitelbaum et al., (1974) Suppression of experimental allergic encephalomyelitis in rhesus monkeys by a synthetic basic copolymer. Clin. Immunol. Immunopathol. 3(2): 256-262.
Teitelbaum et al., (1977) Suppression of experimental allergic encephalomyelitis in baboons by Cop 1. Israeli Med Sci 13: 1038.
Teitelbaum et al., (1988) Specific inhibition of the T-cell response to myelin basic protein by the synthetic copolymer Cop 1. Proc Natl Acad Sci USA 85(24): 9724-9728.
Teitelbaum et al., (1996) Copolymer 1 inhibits chronic relapsing experimental allergic encephalomyelitis induced by proteolipid protein (PLP) peptides in mice and interferes with PLP-specific T cell responses. J Neuroimmunol 64(2): 209-217.
Teitelbaum et al., (2003) Antibodies to glatiramer acetate do not interfere with its biological functions and therapeutic efficacy. Mult Scler 9(6): 592-599.
Tiwari and Verma (2011) Microencapsulation technique by solvent evaporation method (Study of effect of process variables). Int J of Pharm & Life Sci (IJPLS) 2(8): 998-1005.
Tselis et al., (2007) Glatiramer acetate in the treatment of multiple sclerosis. Neuropsychiatr Dis Treat 3(2): 259-267.
Webb et al., (1973) Correlation between strain differences in susceptibility to experimental allergic encephalomyelitis and the immune response to encephalitogenic protein in inbred guinea pigs. Immunol Commun 2(2): 185-192.
Wolinsky and PROMiSe Trial Study Group (2004) The PROMiSe trial: baseline data review and progress report. Mult Scler 10 Suppl 1: S65-S72.
Wolinsky et al., (2007) Glatiramer acetate in primary progressive multiple sclerosis: results of a multinational, multicenter, double-blind, placebo-controlled trial. Ann Neurol 61(1): 14-24.
Wolinsky et al., (2009) Glatiramer acetate treatment in PPMS: why males appear to respond favorably. J Neurol Sci 286(1-2): 92-98.
Wolinsky et al., (2015) GLACIER: An open-label, randomized, multicenter study to assess the safety and tolerability of glatiramer acetate 40 mg three-times weekly versus 20 mg daily in patients with relapsing-remitting multiple sclerosis. Mult Scler Relat Disord 4(4): 370-376.
Ziemssen et al., (2015) Evaluation of Study and Patient Characteristics of Clinical Studies in Primary Progressive Multiple Sclerosis: A Systematic Review. PLoS One 10(9): e0138243; 22 pages.
ClinicalTrials.gov Identifier: NCT02212886. Safety, Tolerability and Efficacy of Monthly Long-acting IM Injection of 80 or 40 mg GA Depot in Subjects With RRMS. Retrieved form: //clinicaltrials.gov/ct2/show/NCT02212886?term=mi+ga+depot++001&rank=1 on Aug. 10, 2016. 7 pages.
COPAXONE®, Highlights of prescribing information; COPAXONE (glatiramer acetate) solution for subcutaneous injection, Initial U.S. Approval: 1996. Revised: Feb. 2009 (Feb. 2009). Marketed by: TEVA Neuroscience, Inc., Kansas City, MO, USA. 22 pages.
COPAXONE®, Highlights of prescribing information; COPAXONE (glatiramer acetate injection) for subcutaneous use, Initial U.S. Approval: 1996. Revised: Aug. 2016 (Aug. 2016). Marketed by: Teva Neuroscience, Inc., Overland Park, KS, USA. 8 pages.
OCREVUSTM (ocrelizumab) injection, for intravenous use Initial U.S. Approval: 2017; Revised: Mar. 2017. Reference ID: 4076448. OCREVUSTM [ocrelizumab], Manufactured by: Genentech, Inc. South San Francisco, CA, USA. The Medication Guide has been approved by the U.S. Food and Drug Administration. 18 pages.
INFORMS (clinical trials: NCT00731692) from the NIH clinical trials website: clinicaltrials.gov/ct2/show/NCT00731692, retrieved on Nov. 21, 2020. 13 pages.
Safety, Tolerability and Efficacy of Monthly Long-acting IM Injection of 80 or 40 mg GA Depot in Subjects With RRMS—Tubular view—ClinicalTrials.gov. Aug. 8, 2014 (Aug. 8, 2014), XP055679718. Retrieved from the Internet: URL: clinicaltrials.gov/ct2/show/record/NCT02212886, on Mar. 25, 2020. 8 pages.
U.S. FDA grants Breakthrough Therapy Designation for Roche's investigational medicine ocrelizumab in primary progressive multiple sclerosis; Investor Update. Basel, Feb. 17, 2016. Retrieved from: www.roche.com/investors/updates/inv-update-2016-02-17.htm on Aug. 29, 2019. 4 pages.
Van Metre et al., (1996) Pain and dermal reaction caused by injected glycerin in immunotherapy solutions. J Allergy Clin Immunol 97(5): 1033-1039.
Varkony et al., (2009) The glatiramoid class of immunomodulator drugs. Expert Opin Pharmacother 10(4): 657-668.
Viglietta Vet al., (2004) Loss of functional suppression by CD4+ CD25+ regulatory T cells in patients with multiple sclerosis. J Exp Med 199(7): 971-979.
Virley (2005) Developing therapeutics for the treatment of multiple sclerosis. NeuroRx 2(4): 638-649.
Weber et al., (2004) Multiple sclerosis: glatiramer acetate inhibits monocyte reactivity in vitro and in vivo. Brain 127(Pt 6): 1370-1378.
Weber et al., (2007) Mechanism of action of glatiramer acetate in treatment of multiple sclerosis. Neurotherapeutics 4 (4): 647-653.
Webster's Ninth New Collegiate Dictionary, Merriam-Webster, Inc., 1985, p. 872, submitted as Exhibit 2027 in Inter Partes Review Case No. IPR2015-00830.
Wekerle et al., (1986) Cellular immune reactivity within the CNS. Trends in Neurosciences 9: 271-277.
Wolinsky (2004) Glatiramer acetate for the treatment of multiple sclerosis. Expert Opin Pharmacother 5(4): 875-891.
Wolinsky (2006) The use of glatiramer acetate in the treatment of multiple sclerosis. Adv Neurol 98: 273-292. Abstract.
Wroblewski (1991) Mechanism of deiodination of 125I-human growth hormone in vivo. Relevance to the study of protein disposition. Biochem Pharmacol 42(4): 889-897.
Wynn et.al., Patient Experience with Glatiramer Acetate 40 mg/1 ml Three-Times Weekly Treatment for Relapsing-Remitting Multiple Sclerosis: Results from the GLACIER Extension Study. Neurology 84 (14 Supplement): P7.218. Presented at The 8th Congress of the Pan-Asian Committee for Treatment and Research in Multiple Sclerosis, Seoul, Republic of Korea (Nov. 19-21, 2015).
Yong (2002) Differential mechanisms of action of interferon-beta and glatiramer aetate in MS. Neurology 59(6): 802-808.

(56) References Cited

OTHER PUBLICATIONS

Zellner et al., (2005) Quantitative validation of different protein precipitation methods in proteome analysis of blood platelets. Electrophoresis 26(12): 2481-2489.
Zhang and Hay (2014a) Cost-effectiveness of Fingolimod, Teriflunomide, Dimethyl Fumarate and Intramuscular Interferon Beta-1a in Relapsing-remitting Multiple Sclerosis. Poster, Monday Morning, PND20, ISPOR 19th Annual International Conference, May 2014, Montreal, Quebec, Canada.
Zhang and Hay (2014b) Cost-effectiveness of Fingolimod, Teriflunomide, Dimethyl Fumarate and Intramuscular Interferon Beta-1a in Relapsing-remitting Multiple Sclerosis. American Society for Health Economics 5th Biennial Conference, Jun. 2014, Los Angeles, CA.
Zhang et al., (2015) Cost effectiveness of fingolimod, teriflunomide, dimethyl fumarate and intramuscular interferon-β1a in relapsing-remitting multiple sclerosis. CNS Drugs 29(1): 71-81.
Ziemssen (2005) Modulating processes within the central nervous system is central to therapeutic control of multiple sclerosis. J Neurol 252 Suppl 5: v38-v45.
Ziemssen and Gilgun-Sherki (2015) Sub-analysis of geographical variations in the 2-year observational COPTIMIZE trial of patients with relapsing-remitting multiple sclerosis converting to glatiramer acetate. BMC Neurol 15: 189.
Ziemssen and Schrempf (2007) Glatiramer acetate: mechanisms of action in multiple sclerosis. Int Rev Neurobiol 79: 537-570.
Ziemssen et al., (2001) Risk-benefit assessment of glatiramer acetate in multiple sclerosis. Drug Saf 24(13): 979-990.
Ziemssen et al., (2002) Glatiramer acetate-specific T-helper 1- and 2-type cell lines produce BDNF: implications for multiple sclerosis therapy. Brain-derived neurotrophic factor. Brain 125(Pt 11): 2381-2391.
Ziemssen et al., (2008) Effects of glatiramer acetate on fatigue and days of absence from work in first-time treated relapsing-remitting multiple sclerosis. Health Qual Life Outcomes 6: 67.
Ziemssen et al., (2008) Presence of Glatiramer Acetate-Specific TH2 Cells in the Cerebrospinal Fluid of Patients with Multiple Sclerosis 12 Months After the Start of Therapy with Glatiramer Acetate, J Neurodegen Regen 1: 19-22.
Ziemssen et al., (2014) A 2-year observational study of patients with relapsing-remitting multiple sclerosis converting to glatiramer acetate from other disease-modifying therapies: the COPTIMIZE trial. J Neurol 261(11): 2101-2111.
Ziemssen et al., (2014) QualiCOP: An Open-Label, Prospective, Observational Study of Glatiramer Acetate in Patients with Relapsing-Remitting Multiple Sclerosis. Retrieved form: http://www.comtecmed.com/cony/2014/Uploads/Editor/Rainer.pdf.
Ziemssen T. (2004) Neuroprotection and Glatiramer Acetate: The Possible Role in the Treatment of Multiple Sclerosis. In: Vécsei L. (eds) Frontiers in Clinical Neuroscience. Advances in Experimental Medicine and Biology, vol. 541., pp. 111-134. Springer, Boston, MA. https://doi.org/10.1007/978-1-4419-8969-7_7.
Zivadinov et al., (2008) Mechanisms of action of disease-modifying agents and brain volume changes in multiple sclerosis. Neurology 71(2): 136-144.
Zivadinov et al., (2015) MRI indicators of brain tissue loss: 3-year results of the Glatiramer Acetate Low-frequency Administration (GALA) open-label extension study in relapsing-remitting multiple sclerosis (P7.255). Neurology 84 (14 Supplement): P7.255. Presented at The American Academy of Neurology 2015 Annual Meeting, Washington, DC (Apr. 18-25, 2015).
Sage Journals, Table of Contents, http://msj.sagepub.com/content/14/1_suppl.toc (Sep. 2008).
Thall and Russell (1998) A strategy for dose-finding and safety monitoring based on efficacy and adverse outcomes in phase I/II clinical trials. Biometrics 54(1): 251-264.
Expanded Disability Status Scale (EDSS) | Multiple Sclerosis Society UK, retrieved from <https://www.mssociety.org.uk/about-ms/treatments-and-therapies/getting-treatment-for-ms/expanded-disability-status-scale>, 7 pages, accessed Sep. 20, 2021.

History of Changes for Study: NCT02212886, Safety, Tolerability and Efficacy of Monthly Long-acting IM Injection of 80 or 40 mg GA Depot in Subjects With RRMS, Dec. 23, 2015, retrieved from <https://clinicaltrials.gov/ct2/history/NCT02212886?V_7=View>, 10 pages, accessed Sep. 21, 2021.
Fisniku et al., (2008) Gray matter atrophy is related to long-term disability in multiple sclerosis. Ann Neurol 64(3): 247-254.
Flechter et al., (2002) Comparison of glatiramer acetate (Copaxone) and interferon β-1b (Betaferon) in multiple sclerosis patients: an open-label 2-year follow-up. J Neurol Sci 197(1-2): 51-55.
Flechter et al., (2002) Copolymer 1 (glatiramer acetate) in relapsing forms of multiple sclerosis: open multicenter study of alternate-day administration. Clin Neuropharmacol 25(1): 11-15.
Ford et al., (2006) A prospective open-label study of glatiramer acetate: over a decade of continuous use in multiple sclerosis patients. Mult Scler 12(3): 309-320.
Franklin M and Franz DN; Drug Absorption, Action, and Disposition. In Remington: The Science and Practice of Pharmacy. Paul Beringer ed., 21st edition (2005). Lippincott Williams & Wilkins. pp. 1142-1170, 1167.
Frenken et al., (1994) Analysis of the efficacy of measures to reduce pain after subcutaneous administration of epoetin alfa. Nephrol Dial Transplant 9(9): 1295-1298.
Frick and Pfenniger; Serono to sell Amgen multiple sclerosis drug [Novantrone] in U.S., Firstword Pharma (Nov. 13, 2002), retrieved on May 27, 2015. http://bit.ly/1QXqhpR.
Fridkis-Hareli et al., (1999) Binding motifs of copolymer 1 to multiple sclerosis- and rheumatoid arthritis-associated HLA-DR molecules. J Immunol 162(8): 4697-4704.
Friese et al., (2006) The value of animal models for drug development in multiple sclerosis. Brain 129(Pt 8): 1940-1952.
Frohman et al., (2006) Multiple sclerosis—the plaque and its pathogenesis. N Engl J Med 354(9): 942-955.
Gagnon Louise; Every-Other-Day Dosing of Glatiramer Acetate Reduces Adverse Reactions with Comparable Efficacy to Daily Dosing: Presented at WCTRMS, Peerview Press, Sep. 21, 2008, http://www.peerviewpress.com/every-other-day-dosing-glatiramer-acetate-reduces-adverse-reactions-comparable-efficacy-daily-dosing-presented-wctrms (last visited Mar. 8, 2016).
Ge et al., (2000) Glatiramer acetate (Copaxone) treatment in relapsing-remitting MS: quantitative MR assessment. Neurology 54(4): 813-817.
Ghose et al., (2007) Transcutaneous immunization with Clostridium difficile toxoid A induces systemic and mucosal immune responses and toxin A-neutralizing antibodies in mice. Infect Immun 75(6): 2826-2832.
Giancarlo Comi, Forte: Results from a phase II, 1-year, Randomized, Double-blind, Parallel-Group, Dose-Comparison Study with Glatiramer Acetate in Relapsing-Remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (ACTRIMS, ECTRIMS, LACTRIMS) (2008).
Giovannoni et al., (2015) Is it time to target no evident disease activity (NEDA) in multiple sclerosis? Mult Scler Relat Disord 4(4): 329-333.
Giuliani et al., (2005) Additive effect of the combination of glatiramer acetate and minocycline in a model of MS. J Neuroimmunol 158(1-2): 213-221.
Gladwell Malcolm; High Prices: How to think about prescription drugs, New Yorker (Oct. 25, 2004), retrieved on Sep. 8, 2012. http://www.newyorker.com/magazine/2004/10/25/high-prices (accessed Feb. 28, 2016).
Glenn et al., (1998) Transcutaneous immunization with cholera toxin protects mice against lethal mucosal toxin challenge. J Immunol 161(7): 3211-3214.
Glenn et al., (2003) Transcutaneous immunization and immunostimulant strategies: capitalizing on the immunocompetence of the skin. Expert Rev Vaccines 2(2): 253-267.
Guideline of Clinical investigation of medicinal products for the treatment of multiple sclerosis EMEA, London Nov. 16, 2006 CPMP/EWP/561/98 Rev .1, pp. 1-12.

(56) References Cited

OTHER PUBLICATIONS

Haines et al., (1998) Linkage of the MHC to familial multiple sclerosis suggests genetic heterogeneity. The Multiple Sclerosis Genetics Group. Hum Mol Genet 7(8): 1229-1234.
Helfand Carly; The top 10 best-selling multiple sclerosis drugs of 2013, Fierce Pharma (Sept. 9, 2014), retrieved on May 27, 2015. http://bit.ly/1UKrIDd.
Helfand Carly; Why is Novartis' Copaxone copy lagging? It's all about coverage, analyst explains. Fierce Pharma (Sep. 11, 2015), http://bit.ly/1ia8BNM.
Herper Matthew; Inside The Secret World of Drug Company Rebates. Forbes Pharma & Healthcare (May 10, 2012), http://www.forbes.com/sites/matthewherper/2012/05/10/why-astrazeneca-gives-insurers-60-discounts-on-nexiums-list-price/#155191dd4fd6.
Hestvik et al., (2008) Multiple sclerosis: glatiramer acetate induces anti-inflammatory T cells in the cerebrospinal fluid. Mult Scler 14(6): 749-758.
Hickey (1991) Migration of hematogenous cells through the blood-brain barrier and the initiation of CNS inflammation. Brain Pathol 1(2): 97-105.
Hickey et al., (1991) T-lymphocyte entry into the central nervous system. J Neurosci Res 28(2): 254-260.
Hong et al., (2005) Induction of CD4+CD25+ regulatory T cells by copolymer-I through activation of transcription factor Foxp3. Proc Natl Acad Sci U S A 102(18): 6449-6454.
Hori et al., (2003) Control of regulatory T cell development by the transcription factor Foxp3. Science 299(5609): 1057-1061.
Imming et al., (2006) Drugs, their targets and the nature and No. of drug targets. Nat Rev Drug Discov 5(10): 821-834 with Corrigenda.
Immunological Responses to Different Doses of Glatiramer Acetate in MS: Analyses from the FORTE Trial, Yong W. v., et al., poster session dated Apr. 28, 2009, presented at the 61st Annual American Academy of Neurology meeting in Seattle, Washington U.S.A.
IMS Health; U.S. Pharmaceutical Market: Trends Issues & Outlook (Sep. 15, 2013).
IMS Institute for Health Informatics; Declining Medicine Use and Costs: for Better or Worse?, Chart Notes (May 2013). 56 pages.
IMS Institute for Health Informatics; Medicine Use and Shifting Costs of Healthcare, Chart Notes (Apr. 2014). 59 pages.
In re Copaxone 40 mg Consolidated Cases, No. 14-01171-GMS, Excerpts from Trial Transcript, D.I. Nos. 282-84, 289-92.
In re Copaxone 40 mg Consolidated Cases, No. 14-01171-GMS, Stipulation and [Proposed] Order Concerning Claim Construction Dispute, D.I. 194 (Feb. 12, 2016).
In re Copaxone 40 mg, No. 1:14-cv-01171-CFC (D. Del.), Trial Tr., ECF No. 282-284, 289-292 (discussing Teva's failed GA Depot) (publicly available). 243 pages.
Introduction to Pharmacokinetics and Pharmacodynamics. In: Concepts in Clinical Pharmacokinetics. 5th edition. Edited by DiPiro et al., 2006. American Society of Health-System Pharmacists. pp. 1-17.
ISR of PCT/IL2010/000679 mailed Dec. 27, 2010.
ISR of PCT/IL2012/050138 mailed Aug. 31, 2012.
Jacobs et al., (2000) Intramuscular interferon beta-1a therapy initiated during a first demyelinating event in multiple sclerosis. CHAMPS Study Group. N Engl J Med 343(13): 898-904.
John J. Jessop, Review and Evaluation of Pharmacology Toxicology Data Original NDA Review (1996) (the 1996 FDA SBOA) (attached as Exhibit A to Exh. 1007).
Johnson et al., (1998) Extended use of glatiramer acetate (Copaxone) is well tolerated and maintains its clinical effect on multiple sclerosis relapse rate and degree of disability. Copolymer 1 Multiple Sclerosis Study Group. Neurology 50 (3): 701-708. Abstract.
Kansara et al., (2009) Subcutaneous Delivery of Small Molecule Formulations: An Insight into Biopharmeutics & Formulation Strategies. Drug Deliv Technol 9(6): 38-43.
Katz et al., (2004) Successful Desensitization to Glatiramer Acetate (Copaxone) in Two Patients with Multiple Sclerosis. abstract No. P156. Annual Meeting of the American College of Allergy, Asthma and Immunology; Nov. 7-12, 2003; New Orleans.
Khan et al., "A phase 3 trial to assess the efficacy and safety of glatiramer acetate injections 40mg administered 3 times a week compared to placebo" Oct. 13, 2012; European Committee for Treatment and Research in Multiple Sclerosis.
Khan et al., (2009) Glatiramer acetate 20mg subcutaneous twice-weekly versus daily injections: results of a pilot, prospective, randomised, and rater-blinded clinical and MRI 2-year study in relapsing-remitting multiple sclerosis. Multiple Sclerosis 15: S249-S250. Abstract P819.
Khan et al., Randomized, prospective, rater-blinded, four-year, pilot study to compare the effect of daily versus every-other-day glatiramer acetate 20 mg subcutaneous injections in relapsing-remitting multiple sclerosis, 14 Multiple Sclerosis, S296 (2008).
Klauer and Zettl (2008) Compliance, adherence and the treatment of multiple sclerosis. J Neurol 255 Suppl 6: 87-92.
Kleiner et al., (2010) Immunological Response to Glatiramer Acetate in MS Patients after Different Pretreatments—The CopImmunoNet Study. Neurology 74 (Suppl 2): A554, abstract P06.178.
Bleich-Kimelman et al., (2015) Pre-clinical studies and evaluation of treatment need of glatiramer acetate depot. Abstract release date: Sep. 23, 2015. Retrieved from <https://onlinelibrary.ectrims-congress.eu/ectrims/2015/31st/115168/nadav.bleich-kimelman.pre-clinical.studies.and.evaluation.of.treatment.need.of.html> on May 16, 2022 (paper copy total 2 pages).
Bleich-Kimelman et al., (2016) Pre-Clinical Studies and Evaluation of Treatment Need of Glatiramer Acetate Depot (Long Acting Injection) (P5.314). Neurology 86 (16 Supplement). 2 pages.
Comi et al., (2011) Phase III dose-comparison study of glatiramer acetate for multiple sclerosis. Ann Neurol 69(1): 75-82.
Clinical Trials, NCT02212886, Jan. 28, 2016, Retrieved from <https://clinicaltrials.gov/ct2/history/NCT02212886?_V_9=View#StudyPageTop> 5 pages.
Prescribing Information, Extavia (Interferon beta-1b) Kit for subcutaneous use Highlights of Prescribing Information (Aug. 2009) (on file with author).
Press Release, Biogen Idec, Inc., Avonex® (Interferon beta-1a) IM Injection (Oct. 2008) (on file with author).
Quintana et al., (2008) Systems biology approaches for the study of multiple sclerosis. J Cell Mol Med 12(4): 1087-1093.
Ramot et al., (2012) Comparative long-term preclinical safety evaluation of two glatiramoid compounds (Glatiramer Acetate, Copaxone(R), and TV-5010, protiramer) in rats and monkeys. Toxicol Pathol 40(1): 40-54.
Randall et al.,; Chapter 5: Approaches the the Analysis of Peptides. Peptide and Protein Drug Delivery, edited by Lee VHL. Marcel Dekker, Inc. New York, USA, 1991. pp. 203-246.
Rebif® Product Label (Jun. 2005).
Rebif® U.S. Product Label (2003).
Reinke Thomas; MS Drug Going Generic Without Making Waves, Managed Care (Jun. 2015), http://bit.ly/1KcyXdE.
Rich et al., (2004) Stepped-care approach to treating MS: a managed care treatment algorithm. J Manag Care Pharm 10(3 Suppl B): S26-S32.
Rothwell et al., (1997) Doctors and patients don't agree: cross sectional study of patients' and doctors' perceptions and assessments of disability in multiple sclerosis. BMJ 314(7094): 1580-1583.
Rovaris et al., (2008) Cognitive impairment and structural brain damage in benign multiple sclerosis. Neurology 71(19): 1521-1526.
Rubinchik et al., (1998) Responsiveness of human skin mast cells to repeated activation: an in vitro study. Allergy 53 (1): 14-19.
Rumrill (2009) Multiple Sclerosis: Medical and Psychosocial Aspects, Etiology, Incidence, and Prevalence. Journal of Vocational Rehabilitation 31(2): 75-82.
Ryan and Majno (1977) Acute inflammation. A review. Am J Pathol 86(1): 183-276.
Schmeisser et al., (2000) Radioiodination of human interferon-α2 interferes with binding of C-terminal specific antibodies. J Immunol Methods 238(1-2): 81-85.
Schrempf and Ziemssen (2007) Glatiramer acetate: mechanisms of action in multiple sclerosis. Autoimmun Rev 6(7): 469-475.

(56) References Cited

OTHER PUBLICATIONS

Selection of Injection Volume. In: Pharmaceutical Preformulation and Formulation; A Practical Guide from Candidate Drug Selection to Commercial Dosage Form. 2nd edition, 2009. Edited by Gibson M. informa healthcare, p. 326.
Shalit et al., (1996) Abstract 650, Copolymer-1 (Copaxone®) Induces a Non-Immunologic Activation of Connective Tissue Type Mast Cells, 97 J. Allergy & Clinical Immunology 97(1): part 3 (Peroutka Dep. Ex. 12).
Shaw Gina; Exorbitant Drug Costs May Price Out Patients. The Washington Diplomat (Uploaded: Apr. 27, 2011). Retrieved on Jan. 26, 2016. 3 pages.
Shire et al., (2004) Challenges in the development of high protein concentration formulations. J Pharm Sci 93(6): 1390-1402. Abstract.
Simpson et al., (2002) Glatiramer Acetate—A Review of its use in Relapsing-Remitting Multiple Sclerosis. Adis Drug Evaluation; CNS Drugs 16(12): 825-850.
Simpson et al., (2002) Glatiramer acetate: a review of its use in relapsing-remitting multiple sclerosis. CNS Drugs 16 (12): 825-850.
Singer et al., (2012) Comparative injection-site pain and tolerability of subcutaneous serum-free formulation of interferonβ-1a versus subcutaneous interferonβ-1b: results of the randomized, multi-center, Phase IIIb REFORMS study. BMC Neurol 12: 154.
Soares et al., (2006) Localized panniculitis secondary to subcutaneous glatiramer acetate injections for the treatment of multiple sclerosis: a clinicopathologic and immunohistochemical study. J Am Acad Dermatol 55(6): 968-974.
Sodoyez et al., (1980) 125l-insulin: kinetics of interaction with its receptors and rate of degradation in vivo. Am J Physiol 239(1): E3-E8.
Sorensen et al., (2003) Clinical importance of neutralising antibodies against interferon beta in patients with relapsing-remitting multiple sclerosis. Lancet 362(9391): 1184-1191.
Staton Tracy; Sanofi tags newly OK'd MS drug Lemtrada at $158K, ready to tout head-to-head Rebif data, Fierce Pharma Marketing (Nov. 17, 2014), retrieved on May 27, 2015. http://bit.ly/1QDKTIZ.
Stedman's Medical Dictionary for Health Professions and Nursing; Illustrated 6th edition (2008). Wolter Kluwer; Lippincott Williams & Wilkins. p. 1337.
Stewart and Tran (2012) Injectable multiple sclerosis medications: a patient survey of factors associated with injection-site reactions. Int J MS Care 14(1): 46-53.
Stuart (2004) Clinical management of multiple sclerosis: the treatment paradigm and issues of patient management. J Manag Care Pharm 10(3 Suppl B): S19-S25.
Sumowski et al., (2013) Brain reserve and cognitive reserve in multiple sclerosis: what you've got and how you use it. Neurology 80(24): 2186-2193.
Sustained-release Injectable Products, compiled by J. Senior, Chemistry Industry Press, First version in Sep. 2005, p. 88. Translation of relevant portions.
Table: Approval Timeline, Multiple Sclerosis Drugs. 2015.
Teva News Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis (Jul. 1, 2013). Retrieved on May 22, 2015. 6 pages.
Teva News Release; New Study Demonstrated Significant Reduction in Annualized Relapse Rate and Halting of Disability Progression in MS Patients Switching to Copaxone® (Apr. 14, 2011). 5 pages.
Teva Press Release, Teva Reports First Quarter 2015 Results (Apr. 30, 2015).
Teva Provides Update on Forte Trial (Jul. 7, 2008).
Teva Provides Update on Forte Trial (Jul. 7, 2008). 2 pages.
Teva Provides Update on Forte Trial Jerusalem, Israel (Jul. 7, 2008).
Teva's Shared Solutions® How to Prepare for Your Injection, http://www.copaxone.com/injection-assistance/preparing-your-injection.html (last visited Mar. 7, 2016).
The National MS Society (USA) 2010. Available from: http://www.nationalmssociety.org/about-multiple-sclerosis/what-we-know-about-ms/treatments/index.aspx. Retrieved from: https://web.archive.org/web/20100204190658/http://www.nationalmssociety.org/about-multiple-sclerosis/what-we-know-about-ms/treatments/index.aspx.
Thrower (2007) Clinically isolated syndromes: predicting and delaying multiple sclerosis. Neurology 68(24 Suppl 4): S12-S15. Abstract.
Tintore et al., (2006) Baseline MRI predicts future attacks and disability in clinically isolated syndromes. Neurology 67 (6): 968-972.
Toutain and Bousquet-Mélou (2004) Plasma terminal half-life. J Vet Pharmacol Ther 27(6): 427-439.
Tremlett et al., (2008) Relapses in multiple sclerosis are age- and time-dependent. J Neurol Neurosurg Psychiatry 79 (12): 1368-1374.
Tysabri® Product Label (Oct. 2008).
U.S. Dep't Health & Human Servs., Common Terminology Criteria for Adverse Events (CTCAE) (Published: May 28, 2009 (v4.03: Jun. 14, 2010)). 196 pages.
Valeant Pharms. Int'l, Inc., Transcript of Jun. 17, 2014 Investor Presentation, http://1.usa.gov/21PTRZK.
Valenzuela et al., (2007) Clinical response to glatiramer acetate correlates with modulation of IFN-γ and IL-4 expression in multiple sclerosis. Mult Scler 13(6): 754-762.
Abramsky et al., (1982) Alpha-fetoprotein suppresses experimental allergic encephalomyelitis. J Neuroimmunol 2(1): 1-7.
Aharoni et al., (1998) Bystander suppression of experimental autoimmune encephalomyelitis by T cell lines and clones of the Th2 type induced by copolymer 1. J. Neuroimmunol. 91(1-2): 135-146.
Aharoni et al., (2005) The immunomodulator glatiramer acetate augments the expression of neurotrophic factors in brains of experimental autoimmune encephalomyelitis mice. Proc Natl Acad Sci USA 102(52): 19045-19050.
Aharoni et al., (2008) Demyelination arrest and remyelination induced by glatiramer acetate treatment of experimental autoimmune encephalomyelitis. Proc Natl Acad Sci USA 105(32): 11358-11363.
Anderson and Shive (1997) Biodegradation and biocompatibility of PLA and PLGA microspheres. Adv Drug Deliv Rev 28(1): 5-24.
Armstrong et al., (1997) A novel synthesis of disubstituted ureas using titanium (IV) isopropoxide and sodium borohydride. Tetrahedron Letters 38(9): 1531-1532.
Artuso et al., (2007) Preparation of mono-, di-, and trisubstituted ureas by carbonylation of aliphatic amines with S,S-dimethyl dithiocarbonate. Synthesis 22: 3497-3506.
Bari (2010) A prolonged release parenteral drug delivery system—an overview. Int J Pharm Rev and Res 3(1): 1-11.
Barun and Bar-Or (2011) Treatment of multiple sclerosis with anti-CD20 antibodies. Clin Immunol 142(1): 31-37.
Ben-Nun et al., (1996) The autoimmune reactivity to myelin oligodendrocyte glycoprotein (MOG) in multiple sclerosis is potentially pathogenic: effect of copolymer 1 on MOG-induced disease. J Neurol 243(4 Suppl 1): S14-S22.
Blanchette and Neuhaus (2008) Glatiramer acetate: evidence for a dual mechanism of action. J Neurol 255 Suppl 1: 26-36.
Bleich Kimelman et al., "Glatiramer Acetate Depot: Towards Clinical Application". International Joint Israel-Greek-Italian Neuroimmunological Meeting (ISNI), Elounda, Crete, Greece Jun. 11-14, 2015. Presentation; 25 pages.
Bleich Kimelman et al., "Pre-clinical studies and evaluation of treatment need of glatiramer acetate depot". Presented at the 31st Congress of the European Committee for Treatment and Research in Multiple Sclerosis (ECTRIMS) 2015: Oct. 7-10, Barcelona, Spain. Retrieved from: http://www.mapi-pharma.com/wp-content/uploads/2015/10/ECTRIMS-Barcelona-Oct.-8-2015-Mapi-Pharma-Poster.pdf. Poster; 1 page.
Bleich Kimelman et al., "Pre-Clinical Studies and Evaluation of Treatment Need of Glatiramer Acetate Depot (Long Acting Injection of GA)". The 68th Meeting of the Annual American Academy of Neurology (AAN), Apr. 15-21, 2016, Vancouver, Canada. Poster; 1 page.
Bodmer et al., (1992) Factors influencing the release of peptides and proteins from biodegradable parenteral depot systems. Journal of Controlled Release 21(1-3): 129-137.

(56) References Cited

OTHER PUBLICATIONS

Bolton et al., (1982) Immunosuppression by cyclosporin A of experimental allergic encephalomyelitis. J Neurol Sci 56 (2-3): 147-153.
Bomprezzi et al., (2011) Glatiramer acetate-specific antibody titres in patients with relapsing/remitting multiple sclerosis and in experimental autoimmune encephalomyelitis. Scand J Immunol 74(3): 219-226 with Corrigendum.
Bornstein et al. 1990, Clinical trials of Cop 1 in multiple sclerosis, in Handbook of Multiple Sclerosis, ed. Cook S.D. Marcel Dekker, Inc., pp. 469-480.
Bouissou et al., (2006) The Influence of Surfactant on PLGA Microsphere Glass Transition and Water Sorption: Remodeling the Surface Morphology to Attenuate the Burst Release. Pharmaceutical Research 23(6): 1295-1305.
Brenner et al., (2001) Humoral and cellular immune responses to Copolymer 1 in multiple sclerosis patients treated with Copaxone. J Neuroimmunol 115(1-2): 152-160.
Bright et al., (1999) Tyrphostin B42 inhibits IL-12-induced tyrosine phosphorylation and activation of Janus kinase-2 and prevents experimental allergic encephalomyelitis. J Immunol 162(10): 6255-6262.
Brown (2005) Expert Opinion on Drug Delivery. Informa Healthcare, GB 2(1): 29-42.
Cohen et al., (2007) Randomized, double-blind, dose-comparison study of glatiramer acetate in relapsing-remitting MS. Neurology 68(12): 939-944.
Constantinescu et al., (2011) Experimental autoimmune encephalomyelitis (EAE) as a model for multiple sclerosis (MS). Br J Pharmacol 164(4): 1079-1106.
Correale et al., (2017) Progressive multiple sclerosis: from pathogenic mechanisms to treatment. Brain 140(3): 527-546.
Doshi and Chataway (2016) Multiple sclerosis, a treatable disease. Clin Med (Lond) 16(Suppl 6): s53-s59.
Fridkis-Hareli (2013) Design of Peptide Immunotherapies for MHC Class-II-Associated Autoimmune Disorders. Clin Dev Immunol. 2013: 826191; 24 pages.
Fridkis-Hareli et al., (1999) Binding of random copolymers of three amino acids to class II MHC molecules. Int Immunol 11(5): 635-641.
Goodson JM: Dental applications; in Langer LS, Wise DL (eds): Medical Applications of Controlled Release. Boca Raton, CRC Press, 1984, vol. 2, pp. 115-138.
Hawker (2011) Progressive multiple sclerosis: characteristics and management. Neurol Clin 29(2): 423-434.
Johnson et al., (1995) Copolymer 1 reduces relapse rate and improves disability in relapsing-remitting multiple sclerosis. Results of a phase III multicenter, double-blind, placebo-controlled trial. Neurology 45(7): 1268-1276.
Karussis et al., (2010) Long-term treatment of multiple sclerosis with glatiramer acetate: natural history of the subtypes of antiglatiramer acetate antibodies and their correlation with clinical efficacy. J Neuroimmunol 220(1-2): 125-130.
Khan et al., (2013) Three times weekly glatiramer acetate in relapsing-remitting multiple sclerosis. Ann Neurol 73(6): 705-713.
Kleinman et al., (2010) Medication adherence with disease modifying treatments for multiple sclerosis among US employees. J Med Econ 13(4): 633-640.
Kurtzke (1983) Rating neurologic impairment in multiple sclerosis: an expanded disability status scale (EDSS). Neurology 33(11): 1444-1452.
Langer (1990) Science, American Association for the Advancement of Science, US 249(4976): 1527-1533.
Margolis et al., (2011) Disease-modifying drug initiation patterns in commercially insured multiple sclerosis patients: a retrospective cohort study. BMC Neurol 11: 122; 10 pages.
McKay et al., (2015) Risk factors associated with the onset of relapsing-remitting and primary progressive multiple sclerosis: a systematic review. Biomed Res Int 2015: 817238; 11 pages.
Miller et al., "Glatiramer acetate depot (extended-release) phase IIa one-year study in patients with relapsing remitting multiple sclerosis: safety, tolerability and efficacy (NEDA) analysis". 7th Joint ECTRIMS-ACTRIMS Meeting Oct. 25-28, 2017, Paris, France. Abstract; 2 pages.
Miller et al., "Glatiramer acetate depot (extended-release) phase IIa one-year study in patients with relapsing remitting multiple sclerosis: safety, tolerability and efficacy (NEDA) analysis". 7th Joint ECTRIMS-ACTRIMS Meeting Oct. 25-28, 2017, Paris, France. Poster; 1 page.
Miller et al., "Glatiramer Acetate Depot (extended-release) Phase IIA study in patients with Relapsing Remitting Multiple Sclerosis: Six months' interim analysis". 7th Joint ECTRIMS-ACTRIMS Meeting Oct. 25-28, 2017, Paris, France. Poster; 1 page.
Milo and Miller (2014) Revised diagnostic criteria of multiple sclerosis. Autoimmun Rev 13(4-5): 518-524.
Montalban et al., (2017) Ocrelizumab versus Placebo in Primary Progressive Multiple Sclerosis. N Engl J Med 376(3): 209-220.
Nyska et al., (2014) Histopathology of biodegradable polymers: challenges in interpretation and the use of a novel compact MRI for biocompatibility evaluation. Polym Adv Technol 25(5): 461-467.
O'Riordan et al., (1998) The prognostic value of brain MRI in clinically isolated syndromes of the CNS. A 10-year follow-up. Brain 121 (Pt 3): 495-503.
Oleen-Burkey et al., (2011) The relationship between alternative medication possession ratio thresholds and outcomes: evidence from the use of glatiramer acetate. J Med Econ 14(6): 739-747.
Oraceska et al., "A comparison of dissolution properties from matrix tablets prepared from microcapsules and mixtures containing phenobarbitone and poly(DL-lactic acid)". In: Pharmaceutical Technology, Controlled Drug Release. Wells JI and Rubinstein MH (eds.). Taylor & Francis e-Library, 2005, pp. 141-151.
Polman et al., (2005) Diagnostic criteria for multiple sclerosis: 2005 revisions to the "McDonald Criteria". Ann Neurol 58 (6): 840-846.
Polman et al., (2011) Diagnostic criteria for multiple sclerosis: 2010 Revisions to the McDonald criteria. Ann Neurol 69 (2): 292-302.
Grodowska and Parczewski (2010) Organic solvents in the pharmaceutical industry. Acta Poloniae Pharmaceutica—Drug Research 67(1): 3-12.
Junichi Kira (2016) Latest Multiple Sclerosis Treatment. Journal of the Japanese Society of Internal Medicine 105(5): 894-904. With machine English translation of details and abstract.

* cited by examiner

METHOD FOR SUPPRESSING OR ALLEVIATING PRIMARY OR SECONDARY PROGRESSIVE MULTIPLE SCLEROSIS (PPMS OR SPMS) USING A SUSTAINED RELEASE DEPOT FORMULATION COMPRISING GLATIRAMER ACETATE

CROSS-REFERENCE TO RELATED APPLICATIONS

The present application is a Continuation of U.S. patent application Ser. No. 16/497,120 filed on Sep. 24, 2019 and issued as U.S. Pat. No. 11,167,003, which is a national stage filing under 35 U.S.C. § 371 of PCT/IL2018/050340, filed on Mar. 25, 2018, and claims the benefit of priority to U.S. Provisional Application No. 62/476,794, filed on Mar. 26, 2017. Each application is incorporated herein by references in their entirety.

FIELD OF THE INVENTION

The present invention relates to depot formulations and other implantable systems for prolonged release of glatiramer acetate or other pharmaceutically acceptable salts of glatiramer for treating primary progressive multiple sclerosis (PPMS) and secondary progressive multiple sclerosis (SPMS).

BACKGROUND OF THE INVENTION

Copolymer-1, also known as glatiramer acetate (GA) and marketed under the tradename Copaxone®, comprises the acetate salts of random copolymers of four amino acids, namely L-glutamic acid, L-alanine, L-tyrosine and L-lysine. Glatiramer acetate is the acetate salt of a mixture of synthetic polypeptides, each of which consists essentially of the four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate is 5,000-9,000 Daltons. Glatiramer acetate is sold in USA as Copaxone®, indicated for reduction of the frequency of relapses in patients with Relapsing-Remitting Multiple Sclerosis (RRMS).

Copaxone® has been approved since 1996 for treating relapsing-remitting multiple sclerosis (RRMS) at a dose of 20 mg administered by daily subcutaneous injections. Since 2014, Copaxone® has also been approved at a dose of 40 mg administered by three injections per week, performed at least 48 hours apart. Compared to daily administration of Copaxone® in the 20 mg dose, the latter dose and regime reduce the yearly number of injections by about 200, while maintaining the same efficacy.

Daily and thrice-weekly Copaxone® treatments involve self-injection of the active substance. Frequently observed injection-site problems include irritation, hypersensitivity, inflammation, pain and even necrosis (in the case of interferon 1β treatment) and consequent problems in patient compliance. Side effects generally include a lump at the injection site (injection site reaction), aches, fever, and chills. These side effects are generally mild in nature. Occasionally a reaction occurs minutes after injection in which there is flushing, shortness in breath, anxiety and rapid heartbeat. These side effects subside within thirty minutes. Over time, a visible dent at the injection site due to the local destruction of fat tissue, known as lipoatrophy, may develop. Therefore, an alternative method of administration is desirable. Several serious side effects have been reported for glatiramer acetate, according to the FDA's prescribing label, these include serious side effects to the body's cardiovascular system, digestive system (including liver), hemic and lymphatic system, musculoskeletal system, nervous system, respiratory system, special senses (in particular the eyes), urogenital system; also reported have been metabolic and nutritional disorders; however a link between glatiramer acetate and these adverse effects has not been definitively established (FDA Copaxone® label).

The parenteral route by intravenous (IV), intramuscular (IM), or subcutaneous (SC) injection is the most common and effective form of delivery for small as well as large molecular weight drugs. However, pain, discomfort and inconvenience due to needle sticks makes this mode of drug delivery the least preferred by patients. Therefore, any drug delivery technology that can at a minimum reduce the total number of injections is preferred. Such reductions in frequency of drug dosing in practice may be achieved through the use of injectable depot formulations that are capable of releasing drugs in a slow but predictable manner and consequently improve compliance. For most drugs, depending on the dose, it may be possible to reduce the injection frequency from daily to once or twice monthly or even longer (6 months). In addition to improving patient comfort, less frequent injections of drugs in the form of depot formulations have been shown to reduce unwanted events, such as immunogenicity etc. often associated with large molecular weight drugs.

Microparticles, implants and gels are the most common forms of biodegradable polymeric devices used in practice for prolonging the release of drugs in the body. Microparticles are suspended in an aqueous media right before injection and one can load as much as 40% solids in suspensions. Implant/rod formulations are delivered to SCAM tissue with the aid of special needles in the dry state without the need for an aqueous media. This feature of rods/implants allows for higher masses of formulation, as well as drug content to be delivered. Further, in the rods/implants, the initial burst problems are minimized due to much smaller area in implants compared to the microparticles. Besides biodegradable systems, there are non-biodegradable implants and infusion pumps that can be worn outside the body. Non-biodegradable implants require a doctor's visit not only for implanting the device into the SC/IM tissue but also to remove them after the drug release period.

Injectable compositions containing microparticle preparations are particularly susceptible to problems. Microparticle suspensions may contain as much as 40% solids as compared with 0.5-5% solids in other types of injectable suspensions. Further, microparticles used in injectable depot products, range in size up to about 250 μm (average, 60-100 μm), as compared with a particle size of less than 5 μm recommended for IM or SC administration. The higher concentrations of solids, as well as the larger solid particle size require larger size of needle (around 18-21 gauge) for injection. Overall, despite the infrequent uses of larger and uncomfortable needles, patients still prefer the considerably less frequently administered dosage forms over more frequent administration regimens such as every day or thrice weekly drug injections with a smaller needle.

Biodegradable polyesters of poly(lactic acid) (PLA) and copolymers of lactide and glycolide referred to as poly (lactide-co-glycolide) (PLGA) are the most common polymers used in biodegradable dosage forms. PLA is hydrophobic molecule and PLGA degrades faster than PLA because of the presence of more hydrophilic glycolide groups. These biocompatible polymers undergo random, non-enzymatic, hydrolytic cleavage of the ester linkages to form lactic acid and glycolic acid, which are normal metabolic compounds in the body. Resorbable sutures, clips and implants are the earliest applications of these polymers. Southern Research Institute developed the first synthetic, resorbable suture (Dexon®) in 1970. The first patent describing the use of PLGA polymers in a sustained release dosage form appeared in 1973 (U.S. Pat. No. 3,773,919).

Today, PLGA polymers are commercially available from multiple suppliers. Besides PLGA and PLA, natural cellulosic polymers such as starch, starch derivatives, dextran and non-PLGA synthetic polymers are also being explored as biodegradable polymers in such systems.

U.S. Pat. Nos. 8,377,885 and 8,796,226 to some of the present inventors relate to long acting pharmaceutical compositions comprising glatiramer acetate in depot form.

Ocrelizumab (OCREVUS™) is a humanized anti-CD20 monoclonal antibody, which was granted Breakthrough Therapy Designation for PPMS by the Food and Drug Administration (FDA) in 2016. It was approved by the FDA in 2017 as a treatment for multiple sclerosis, and it is the first FDA-approved drug for PPMS. It is administered by intravenous infusion.

To date, no long acting dosage forms of glatiramer acetate are commercially available for treating MS patients. An ongoing clinical trial is being conducted to test safety and/or efficacy of depot forms of GA in relapsing remitting forms of MS. There is an unmet medical need in treatment options for progressive forms of MS. Preferably, such treatments would be administered in depot formulations, to minimize the frequency of drug-delivery steps and associated side-effects.

SUMMARY OF THE INVENTION

The present invention provides a method of treating progressive forms of multiple sclerosis (MS) and related symptoms, comprising administration or implantation of a long acting depot formulation of a pharmaceutically acceptable glatiramer salt, e.g., glatiramer acetate. According to various embodiments, the depot formulation is administered once every week, once every several weeks, once a month or once every several months. According to additional embodiments, the depot formulation provides a dose of 10-100 mg of pharmaceutically acceptable salts of glatiramer, e.g., glatiramer acetate, to a patient.

It is now disclosed for the first time that the long acting pharmaceutical compositions and depot formulations according to the principles of the present invention provide therapeutic efficacy in primary progressive multiple sclerosis (PPMS) and secondary progressive multiple sclerosis (SPMS) patients. It has further been unexpectedly found that administration once every several weeks of a depot of 10-100 mg glatiramer acetate according to the principles of the present invention is beneficial to PPMS and SPMS patients.

The present invention provides, in one aspect, a method for treating or alleviating primary progressive multiple sclerosis (PPMS), secondary progressive multiple sclerosis (SPMS) or at least one symptom of PPMS or SPMS, in a patient diagnosed with PPMS or SPMS, using depot formulations of GA. The method comprises the step of administering to the patient a therapeutically effective regimen of a depot formulation comprising glatiramer acetate (GA) or another pharmaceutically acceptable salt of glatiramer, the regimen being sufficient to treat or alleviate PPMS, SPMS or the at least one symptom of PPMS or SPMS. According to certain embodiments the depot formulation comprises glatiramer acetate.

In certain embodiments, the patient has been diagnosed as suffering from PPMS. In certain embodiments, the patient has been diagnosed as suffering from SPMS.

In certain embodiments, treating PPMS or SPMS comprises reducing the rate of progression of PPMS or SPMS. In certain embodiments, treating PPMS or SPMS comprises increasing the time to onset of Confirmed Disease Progression (CDP). In certain embodiments, treating PPMS or SPMS comprises increasing the time to onset of 12 week Confirmed Disease Progression (CDP) assessed by EDSS, compared to baseline. In certain embodiments, treating PPMS or SPMS comprises decreasing whole brain volume change or cortical volume change, compared to baseline. In certain embodiments, treating PPMS or SPMS comprises decreasing the time needed to complete a timed 25-foot walk (T25FW) test, compared to baseline. In certain embodiments, treating PPMS or SPMS comprises decreasing the time needed to complete a 9-Hole Peg Test (9-HPT), compared to baseline.

In certain embodiments, treating PPMS or SPMS comprises decreasing (i) the number of new or enlarging T2 lesions; (ii) the volume of T2 lesions; (iii) the number of new or enlarging T1 lesions; (iv) the volume of T1 lesions; (v) the number or volume of Gadolinium (Gd) lesions; or (vi) any combination of (i) to (v). Each possibility represents a separate embodiment of the invention. In certain embodiments, treating PPMS or SPMS comprises preventing further progression of PPMS or SPMS, compared to baseline.

In certain embodiments, the symptom is selected from the group consisting of impaired coordination, impaired walking capability, impaired balance, weakness of the leg, stiffness of the leg, impaired memory, impaired cognitive function, a difficulty to swallow, impaired vision, general fatigue, pain, impaired bladder function, impaired bowel function, and any combination thereof. Each possibility represents a separate embodiment of the invention.

In certain embodiments, the depot formulation is administered once every 1 to 15 weeks. In certain embodiments, the depot formulation is administered once every 2 to 6 weeks. According to some embodiments, the administration comprises an injection of the depot formulation once every 2 to 6 weeks. In certain embodiments, the depot formulation is administered once every 4 weeks. According to some embodiments, the administration comprises intramuscular injection of the depot formulation once every 4 weeks.

In certain embodiments, the depot formulation is parenterally administered. In certain embodiments, the depot formulation is administered by intramuscular, subcutaneous, percutaneous, intravenous, or inhalation administration. Each possibility represents a separate embodiment of the invention. In certain embodiments, the depot formulation is intramuscularly administered. In certain embodiments, the depot formulation is subcutaneously administered.

In certain embodiments, the depot formulation is administered in a concentration of 20 mg GA per 1 mL of a carrier. In certain embodiments, the carrier is water for injection (WFI). In certain embodiments, the depot formulation comprises 20% to 30% solids. In certain embodiments, the depot formulation comprises a Poly(Lactide-co-Glycolide) (PLGA) copolymer. In certain embodiments, the PLGA copolymer is a poly(D,L-lactide-co-glycolide) (50:50) copolymer. In certain embodiments, the depot formulation comprises 550 mg PLGA copolymer per 40 mg of GA. In certain embodiments, the PLGA copolymer at least partly encapsulates the GA. In certain embodiments, the depot formulation comprises a 40 to 80 mg dose of GA. In certain embodiments, the depot formulation comprises a 40 mg dose of GA. In certain embodiments, the depot formulation comprises an 80 mg dose of GA.

In certain embodiments, less than 45% of the GA is released from the depot formulation within 14 days in PBS at 37° C. under continuous agitation. In certain embodiments, more than 90% of the GA is released from the depot formulation within 28 days in PBS at 37° C. under continuous agitation.

In certain embodiments, the patient (i) has been diagnosed with PPMS or SPMS for at least 1 year and a sustained increment of ≥1 point in the EDSS score in the last year or ≥0.5 points in EDSS score; (ii) has an EDSS score between 2 and 5.5, inclusive; (iii) has a documented history of, or the presence of more than 1 oligoclonal band (OCB) (IgG OCB positive (OCGB+)) and/or positive IgG index in the cerebrospinal fluid (CSF); (iv) has at least 1 gadolinium-enhancing lesion on MRI and/or at least 1 gadolinium-enhancing lesion documented within a previous year on MRI; or (v) any combination of (i) to (iv). Each possibility represents a separate embodiment of the invention. In certain embodiments, the patient has at least two separate areas of damage in the central nervous system (CNS) that have occurred at different points in time. In certain embodiments, the patient has a history of at least one year of disease progression, and at least two from the group consisting of (i) at least one area of damage in the CNS, (ii) at least two areas of damage of a similar type in the spinal cord, and (iii) oligoclonal band in the spinal fluid or an elevated IgG index. In certain embodiments, the patient has no history of relapse events. In certain embodiments, the patient has no history of remission events. In certain embodiments, the patient has not received GA therapy prior to initiation of the regimen of the present invention. In certain embodiments, the patient has received GA therapy prior to initiation of the regimen of the present invention. In certain embodiments, the patient has received daily GA therapy prior to initiation of the regimen of the present invention. In certain embodiments, the patient has received thrice weekly GA therapy prior to initiation of the regimen of the present invention.

In certain embodiments, a plurality of administrations of the depot formulations of the invention is provided to the subject in need thereof. In certain embodiments, the regimen is repeated at least twice. In certain embodiments, the regimen is consecutively repeated for at least 6 months. In certain embodiments, the regimen is consecutively repeated for at least 1 year.

In certain embodiments, the frequency of administration is reduced relative to daily administration of 20 mg GA or a thrice weekly administration of 40 mg GA. In certain embodiments, the dose of GA administrated is reduced relative to daily administration of 20 mg GA or a thrice weekly administration of 40 mg GA. Each possibility represents a separate embodiment of the invention.

The present invention further provides, in another aspect, a method of increasing the tolerability of a patient suffering from primary progressive multiple sclerosis (PPMS) or secondary progressive multiple sclerosis (SPMS) to GA treatment, the method comprising reducing the frequency of GA administration to a therapeutically effective regimen of a depot formulation of GA or another pharmaceutically acceptable salt of glatiramer, so as to thereby increase the tolerability of GA treatment in the patient.

In certain embodiments, increasing the tolerability of GA treatment comprises reducing the frequency of injections. In certain embodiments, increasing the tolerability of GA treatment comprises reducing the frequency of an injection site reaction. In certain embodiments, increasing the tolerability of GA treatment comprises reducing the total dose of GA administered over a period of time. In certain embodiments, increasing the tolerability of GA treatment comprises improving patient compliance.

The present invention further provides, in another aspect, a method of increasing the convenience of GA treatment of a patient suffering from primary progressive multiple sclerosis (PPMS) or secondary progressive multiple sclerosis (SPMS) by decreasing the administration frequency of GA. The method comprises reducing the frequency of administrations by instituting a therapeutically effective regimen of a depot formulation of GA or another pharmaceutically acceptable salt of glatiramer, so as to thereby increase the convenience of GA treatment of the patient.

The present invention further provides, in another aspect, a method of increasing the adherence to GA treatment of a patient suffering from primary progressive multiple sclerosis (PPMS) or secondary progressive multiple sclerosis (SPMS), the method comprising reducing the frequency of administrations of GA by instituting a therapeutically effective regimen of a depot formulation of GA or another pharmaceutically acceptable salt of glatiramer, so as to thereby increase the adherence to GA treatment of the patient.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
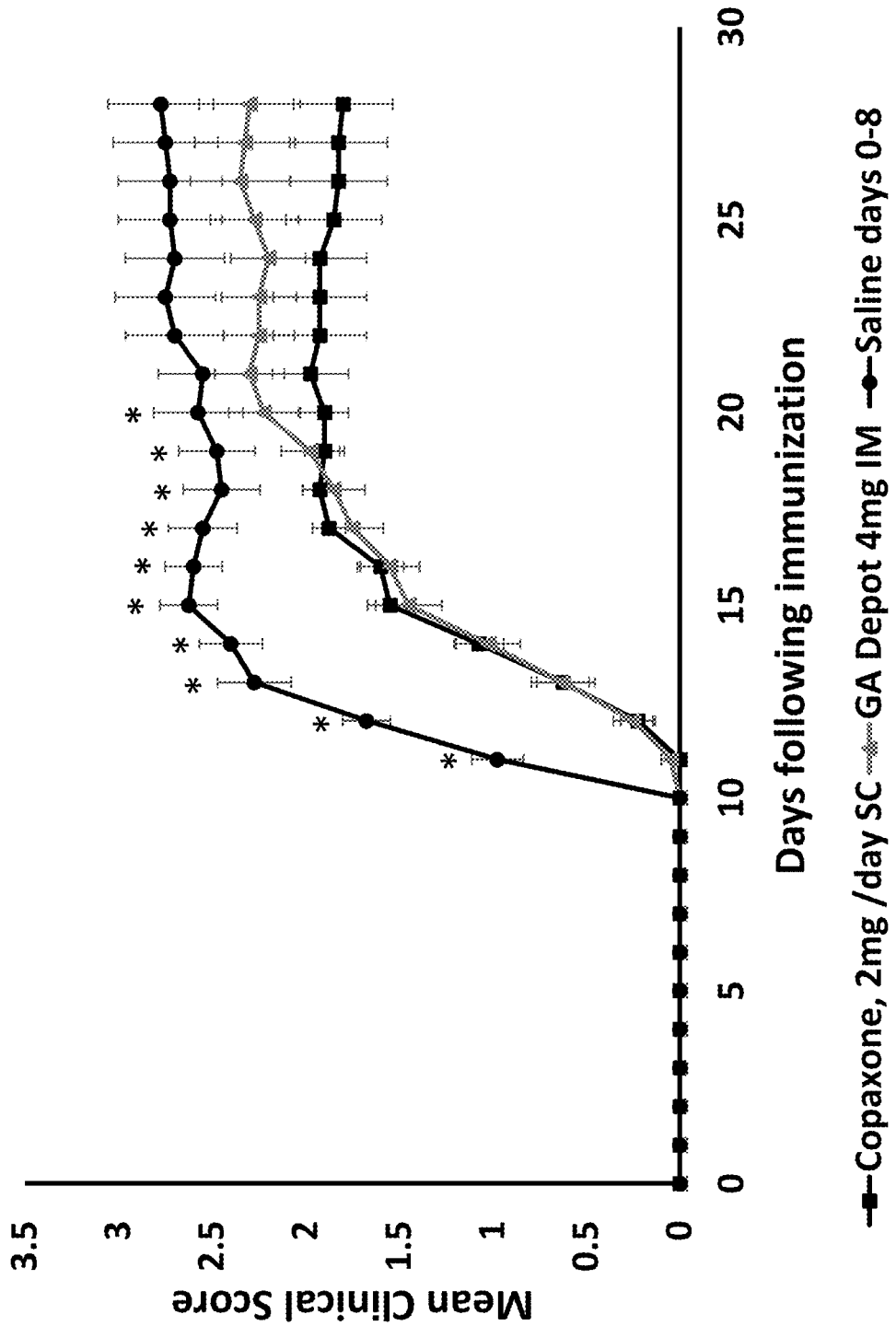
FIG. 1 illustrates the mean clinical score results for saline control, Copaxone® (2 mg GA, days 0-8) and GA Depot (4 mg GA, day 0) in C57BL/6 mice groups. *P<0.05 for all treatment groups compared with untreated control, Single Factor ANOVA followed by one-tailed T Test assuming unequal variance. N=20/group, +/−standard error.

The present invention provides long acting depot formulations of glatiramer acetate (GA), with significant therapeutic efficacy in PPMS or SPMS patients, and reduced side effects resulting from infrequent GA administrations.

The invention is based on the surprising finding that GA, previously deemed ineffective in multiple clinical studies of PPMS patients, is indeed effective in treating PPMS and SPMS patients when formulated as depot systems and administered in lower-than-expected doses.

The present invention provides, in one aspect, a method for treating or alleviating PPMS or SPMS or at least one symptom of PPMS or SPMS in a patient diagnosed with PPMS or SPMS, the method comprising the step of administering to the patient a therapeutically effective regimen of a depot formulation comprising glatiramer acetate (GA) or another pharmaceutically acceptable salt of glatiramer, the regimen being sufficient to treat or alleviate PPMS or SPMS or the at least one symptom of PPMS or SPMS.

According to the principles of the present invention, the phrase "patient diagnosed as suffering from PPMS" or the term "PPMS patient" as used interchangeably herein refer to a patient diagnosed as suffering from PPMS, i.e. in a progressive phase of MS. According to the principles of the present invention, the phrase "patient diagnosed as suffering from SPMS" or the term "SPMS patient" as used interchangeably herein refer to a subject diagnosed as suffering from SPMS, i.e. after a relapsing-remitting phase has practically ended, after a progressive phase began, and in a progressive phase of MS.

In certain embodiments, the patient has been diagnosed as suffering from PPMS. In certain embodiments, the patient diagnosed as suffering from PPMS is in a progressive phase of PPMS. In certain embodiments, the patient has been diagnosed as suffering from SPMS. In certain embodiments, the patient diagnosed as suffering from SPMS is in a progressive phase of SPMS.

The term "therapeutically effective regimen" as used herein is intended to qualify the frequency of administration and the amount of GA that will achieve the goal of treatment or alleviation of PPMS or SPMS, or of treatment or alleviation of a symptom of PPMS or SPMS. The term "depot formulation" as used herein refers to a composition which provides prolonged, sustained or extended release of the glatiramer salt to the general systemic circulation of a subject or to local sites of action in a subject. This term may further refer to a composition which provides prolonged, sustained or extended duration of action (pharmacokinetics) of the glatiramer salt in a subject. The term "treating" as used herein refers to prevention, suppression or alleviation of a symptom or of a plurality of symptoms after the onset of PPMS or SPMS.

The term "glatiramer acetate" as used herein refers to a compound formerly known as Copolymer 1 that is sold under the trade name Copaxone® and consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate in Copaxone® is 4,700-11,000 daltons (FDA Copaxone® label) and the number of amino acid ranges between about 15 to about 100 amino acids. The term also refers to chemical derivatives and analogues of the compound. Typically the compound is prepared and characterized as specified in any of U.S. Pat. Nos. 5,981,589; 6,054,430; 6,342,476; 6,362,161; 6,620,847; and 6,939,539, the contents of each of these references are hereby incorporated in their entirety.

The copolymers can be made by any procedure available to one of skill in the art. For example, the copolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example, dicyclohexylcarbodiimide, can be used to facilitate the formation of the peptide bond.

In some embodiments, the composition may comprise any other pharmaceutically acceptable salt of glatiramer including, but not limited to, sulfate, pyrosulfate, bisulfate, sulfite, bisulfate, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Each possibility represents a separate embodiment of the invention.

In certain embodiments, the symptom is impaired coordination. In certain embodiments, the symptom is impaired walking capability. In certain embodiments, the symptom is impaired balance. In certain embodiments, the symptom is weakness of the leg. In certain embodiments, the symptom is stiffness of the leg. In certain embodiments, the symptom is impaired memory. In certain embodiments, the symptom is impaired cognitive function. In certain embodiments, the symptom is a difficulty to swallow. In certain embodiments, the symptom is impaired vision. In certain embodiments, the symptom is general fatigue. In certain embodiments, the symptom is pain. In certain embodiments, the symptom is impaired bladder function. In certain embodiments, the symptom is impaired bowel function. In certain embodiments, the symptom is a combination of PPMS or SPMS symptoms.

In certain embodiments, the depot formulation is administered once every 1 to 15 weeks. In certain embodiments, the depot formulation is administered once every 1 to 10 weeks. According to some embodiments, the administration comprises an injection. According to some embodiments, the administration comprises an injection every 2 to 6 weeks. According to some embodiments, the administration comprises an administration every 2 to 6 weeks. In certain embodiments, the depot formulation is administered once every 2 weeks. In certain embodiments, the depot formulation is administered once every 3 weeks. In certain embodiments, the depot formulation is administered once every 4 weeks. In certain embodiments, the depot formulation is administered once every 5 weeks. In certain embodiments, the depot formulation is administered once every 6 weeks. In certain embodiments, the depot formulation is parenterally administered. In certain embodiments, the depot formulation is administered by intramuscular, subcutaneous, percutaneous, intravenous, or inhalation administration. Each possibility represents a separate embodiment of the invention. In certain embodiments, the depot formulation is intramuscularly administered. In certain embodiments, the depot formulation is subcutaneously administered.

In certain embodiments, the depot formulation is administered in a concentration of 10 mg GA per 1 mL of a carrier. In certain embodiments, the depot formulation is administered in a concentration of 20 mg GA per 1 mL of a carrier. In certain embodiments, the depot formulation is administered in a concentration of 40 mg GA per 1 mL of a carrier. In certain embodiments, the carrier is WFI. The term "water for injection" or "WFI" as used herein generally means sterile, pure water that meets regulatory standards for e.g. particulates, dissolved solids, organics, inorganics, microbial and endotoxin contaminants. In certain embodiments, the depot formulation is administered in WFI) or a buffer containing a suspending agent (e.g. carboxymethylcellulose, CMC), a buffering agent (e.g. citrate salts) and/or a tonicity agent (e.g. NaCl).

In certain embodiments, the depot formulation comprises 10% to 40% solids. In certain embodiments, the depot formulation comprises 20% to 30% solids. In certain embodiments, the depot formulation comprises a Poly(Lactide-co-Glycolide) (PLGA) copolymer. In certain embodiments, the PLGA copolymer is a poly(D,L-lactide-co-glycolide) (50:50) copolymer. In certain embodiments, the depot formulation comprises 150-1500 mg PLGA copolymer per 40 mg of GA. In certain embodiments, the depot formulation comprises 550 mg PLGA copolymer per 40 mg of GA. In certain embodiments, the PLGA copolymer at least partly encapsulates the GA. In certain embodiments, the PLGA copolymer encapsulates the GA.

In certain embodiments, the depot formulation comprises at least 20 mg dose of GA or of another pharmaceutically acceptable salt thereof. In certain embodiments, the depot formulation comprises between 20 to 1000 mg dose of GA or of another pharmaceutically acceptable salt thereof. In certain embodiments, the depot formulation comprises between 20 to 750 mg dose of GA or of another pharmaceutically acceptable salt thereof. In certain embodiments, the depot formulation comprises 40 to 80 mg dose of GA. In certain embodiments, the depot formulation comprises a 40 mg dose of GA. In certain embodiments, the depot formulation comprises a 50 mg dose of GA. In certain embodiments, the depot formulation comprises a 60 mg dose of GA. In certain embodiments, the depot formulation comprises a 70 mg dose of GA. In certain embodiments, the depot formulation comprises an 80 mg dose of GA.

In certain embodiments, less than 30% of the GA is released from the depot formulation within 7 days in PBS at 37° C. under continuous agitation. In certain embodiments, more than 20% of the GA is released from the depot formulation within 7 days in PBS at 37° C. under continuous agitation. In certain embodiments, less than 45% of the GA is released from the depot formulation within 14 days in PBS at 37° C. under continuous agitation. In certain embodiments, more than 30% of the GA is released from the depot formulation within 14 days in PBS at 37° C. under continuous agitation. In certain embodiments, less than 85% of the GA is released from the depot formulation within 21 days in PBS at 37° C. under continuous agitation. In certain embodiments, more than 40% of the GA is released from the depot formulation within 21 days in PBS at 37° C. under continuous agitation. In certain embodiments, more than 90% of the GA is released from the depot formulation within 28 days in PBS at 37° C. under continuous agitation.

In certain embodiments, in PBS at 37° C. under continuous agitation, (i) about 14% of the glatiramer is released from the depot formulation within 0 days, and/or (ii) about 15% of the glatiramer is released from the depot formulation within 1 day, and/or (iii) about 21% of the glatiramer is released from the depot formulation within 5 days, and/or (iv) about 25% of the glatiramer is released from the depot formulation within 8 days, and/or (v) about 34% of the glatiramer is released from the depot formulation within 13 days, and/or (vi) about 43% of the glatiramer is released from the depot formulation within 15 days, and/or (vii) about 80% of the glatiramer is released from the depot formulation within 22 days, and/or (viii) about 96% of the glatiramer is released from the depot formulation within 27 days, and/or (ix) about 99% of the glatiramer is released from the depot formulation within 32 days. Each possibility and each combination of possibilities represents a separate embodiment of the invention.

In certain embodiments, treating PPMS or SPMS comprises reducing the rate of progression of a PPMS- or SPMS-related symptom. In certain embodiments, treating PPMS or SPMS comprises reducing the rate of progression of PPMS or SPMS. In certain embodiments, treating PPMS or SPMS comprises increasing the time to onset of Confirmed Disease Progression (CDP). In certain embodiments, treating PPMS or SPMS comprises increasing the time to onset of 12 week Confirmed Disease Progression (CDP) assessed by EDSS, compared to baseline. The Kurtzke Expanded Disability Status Scale (EDSS) is a method of quantifying disability in multiple sclerosis. The EDSS quantifies disability in eight Functional Systems (FS) and allows neurologists to assign a Functional System Score (FSS) in each of these. The EDSS measures disability status on a scale ranging from 0 to 10, with higher scores indicating more disability. In certain embodiments, treating PPMS or SPMS comprises decreasing whole brain volume change or cortical volume change, compared to baseline. The T25FW is a quantitative mobility and leg function performance test where the participant is timed while walking for 25 feet. In certain embodiments, treating PPMS or SPMS comprises decreasing the time needed to complete a timed 25-foot walk (T25FW) test, compared to baseline. The 9-HPT is a quantitative test of upper extremity function that measures the time it takes to place 9 pegs into 9 holes and then remove the pegs. In certain embodiments, treating PPMS comprises decreasing the time needed to complete a 9-Hole Peg Test (9-HPT), compared to baseline. The terms "baseline" and "control" are interchangeable, and used herein to refer to a period of time before imitating treatment by the method of the present invention. In certain embodiments, the term "baseline" as used herein further refers to PPMS or SPMS patients which are untreated by the method of the present invention. In certain embodiments, the term "baseline" as used herein refers to a period of 1 year before imitating using the treatment by the method of the present invention.

In certain embodiments, CDP is defined as one or more of the following criteria, confirmed using one or more of the following assessments: sustained EDSS score increased from baseline of ≥1 point if baseline EDSS≤5.5, or ≥0.5 point if Baseline EDSS>5.5. In certain embodiments, CDP is defined as a sustained (≥12 weeks) increase in EDSS from baseline of ≥1.0 points if the baseline EDSS was between 2.0 and 5.5 points or an EDSS increase of ≥0.5 points if the baseline EDSS was >5.5 points.

In certain embodiments, treating PPMS or SPMS comprises decreasing the number of new or enlarging T2 lesions. In certain embodiments, treating PPMS or SPMS comprises decreasing the volume of T2 lesions. In certain embodiments, treating PPMS or SPMS comprises decreasing the number of new or enlarging T1 lesions. In certain embodiments, treating PPMS or SPMS comprises decreasing the volume of T1 lesions. In certain embodiments, treating PPMS or SPMS comprises decreasing the number or volume of Gadolinium (Gd) lesions. In certain embodiments, treating PPMS or SPMS comprises preventing further progression of PPMS or SPMS, compared to baseline.

In certain embodiments, the patient has been diagnosed with PPMS or SPMS for at least 1 year and a sustained increment of ≥1 point in the EDSS score in the last year. In certain embodiments, the patient has an EDSS score between 2 and 5.5, inclusive. In certain embodiments, the patient has a documented history of, or the presence of more than 1 oligoclonal band (OCB) (IgG OCB positive (OCGB+)) and/or positive IgG index in the cerebrospinal fluid (CSF). In certain embodiments, the patient has at least 1 gadolinium-enhancing lesion on MRI and/or at least 1 gadolinium-enhancing lesion documented within a previous year on MRI. In certain embodiments, the patient has at least two separate areas of damage in the central nervous system (CNS) that have occurred at different points in time. In certain embodiments, the patient has a history of at least one year of disease progression, and at least two from the group consisting of (i) at least one area of damage in the CNS, (ii) at least two areas of damage of a similar type in the spinal cord, and (iii) oligoclonal band in the spinal fluid or an elevated IgG index. Each possibility represents a separate embodiment of the invention. In certain embodiments, the patient has no history of relapse events. In certain embodiments, the patient has no history of remission events. In certain embodiments, the patient has not received GA therapy prior to initiation of the regimen. In certain embodiments, the patient has received GA therapy prior to initiation of the regimen.

In certain embodiments, the regimen is repeated. In certain embodiments, the regimen is repeated at least twice. In certain embodiments, the regimen is consecutively repeated for at least 6 months. In certain embodiments, the regimen is consecutively repeated for at least 1 year. In certain embodiments, the regimen is consecutively repeated for the life time of the patient.

In certain embodiments, the frequency of administration is reduced relative to daily administration of 20 mg GA or a thrice weekly administration of 40 mg GA. In certain embodiments, the dose of GA administrated is reduced relative to daily administration of 20 mg GA or a thrice weekly administration of 40 mg GA. Each possibility represents a separate embodiment of the invention. In some embodiments, the compositions of the present invention provide prolonged release or prolonged action of glatiramer in a subject as compared to a substantially similar dose of an immediate release formulation of glatiramer acetate.

The present invention further provides, in another aspect, a method of increasing the tolerability of a patient suffering from primary progressive multiple sclerosis (PPMS) or secondary progressive multiple sclerosis (SPMS) to GA treatment, the method comprising reducing the frequency of GA administration from daily subcutaneous injections of a 20 mg dose of GA or three subcutaneous injections of a 40 mg dose of GA over a period of seven days with at least one day between every injection, to a therapeutically effective regimen of a depot formulation of GA or another pharmaceutically acceptable salt of glatiramer, so as to thereby increase the tolerability of GA treatment in the patient.

In certain embodiments, increasing the tolerability of GA treatment comprises reducing the frequency of injections. In certain embodiments, increasing the tolerability of GA treatment comprises reducing the frequency of an injection site reaction.

The present invention further provides, in another aspect, a method of increasing the convenience of GA treatment of a patient suffering from primary progressive multiple sclerosis (PPMS) or secondary progressive multiple sclerosis (SPMS), the method comprising reducing the frequency of GA administration to a therapeutically effective regimen of a depot formulation of GA or another pharmaceutically acceptable salt of glatiramer, so as to thereby increase the convenience of GA treatment of the patient.

The present invention further provides, in another aspect, a method of increasing the adherence to GA treatment of a patient suffering from primary progressive multiple sclerosis (PPMS) or secondary progressive multiple sclerosis (SPMS), the method comprising reducing the frequency of GA administration to a therapeutically effective regimen of a depot formulation of GA or another pharmaceutically acceptable salt of glatiramer, so as to thereby increase the adherence to GA treatment of the patient.

The present invention further provides, in another aspect, a depot formulation comprising glatiramer acetate (GA) or another pharmaceutically acceptable salt of glatiramer for use in a method for treating or alleviating PPMS, SPMS or at least one symptom of PPMS or SPMS in a patient diagnosed with PPMS or SPMS, the method comprising the step of administering the depot formulation to the patient.

The present invention further provides, in another aspect, a depot formulation comprising glatiramer acetate (GA) or another pharmaceutically acceptable salt of glatiramer for use in a method of increasing the tolerability of a patient suffering from primary progressive multiple sclerosis (PPMS) or secondary progressive multiple sclerosis (SPMS) to GA treatment, the method comprising reducing the frequency of GA administration from daily subcutaneous injections of a 20 mg dose of GA or three subcutaneous injections of a 40 mg dose of GA over a period of seven days with at least one day between every injection, to an administration of the depot formulation.

The present invention further provides, in another aspect, a depot formulation comprising glatiramer acetate (GA) or another pharmaceutically acceptable salt of glatiramer for use in a method of increasing the convenience of GA treatment of a patient suffering from primary progressive multiple sclerosis (PPMS) or secondary progressive multiple sclerosis (SPMS), the method comprising reducing the frequency of GA administration to a therapeutically effective regimen of the depot formulation.

The present invention further provides, in another aspect, a depot formulation comprising glatiramer acetate (GA) or another pharmaceutically acceptable salt of glatiramer for use in a method of increase the adherence to GA treatment of a patient suffering from primary progressive multiple sclerosis (PPMS) or secondary progressive multiple sclerosis (SPMS), the method comprising reducing the frequency of GA administration to a therapeutically effective regimen of the depot formulation.

In certain embodiments, dosage forms include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); poly-anhydrides; poly(sebacic acid) SA; poly(ricenolic acid) RA; poly(fumaric acid), FA; poly(fatty acid dimmer), FAD;

poly(terephthalic acid), TA; poly(isophthalic acid), IPA; poly(p-{carboxyphenoxy}methane), CPM; poly(p-{carboxyphenoxy} propane), CPP; poly(p-{carboxyphenoxy}hexane)s CPH; polyamines, polyurethanes, polyesteramides, polyoithoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) triblock copolymers (PEO—PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment.

In certain embodiments, the biodegradable polymer is a lactic acid-based polymer, more preferably polylactide, or poly (D, L-lactide-co-glycolide) i.e. PLGA. The biodegradable polymer is present in an amount between about 10% to about 98% w/w of the composition. The lactic acid-based polymer has a monomer ratio of lactic acid to glycolic acid in the range of 100:0 to about 0:100, preferably 100:0 to about 10:90 and has an average molecular weight of from about 1,000 to 200,000 Daltons. However, it is understood that the amount of biodegradable polymer is determined by parameters such as the duration of use and the like.

The compositions and formulations of the present invention may further comprise one or more pharmaceutically acceptable excipient(s) selected from, but not limited to, co-surfactants, solvents/co-solvents, water immiscible solvents, water, water miscible solvents, oily components, hydrophilic solvents, emulsifiers, preservatives, antioxidants, anti-foaming agents, stabilizers, buffering agents, pH adjusting agents, osmotic agents, channel forming agents, osmotic adjustment agents, or any other excipient known in the art. Suitable co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment of the invention. Suitable solvents/co-solvents include, but not limited to, alcohols, triacetin, dimethyl isosorbide, glycofurol, propylene carbonate, water, dimethyl acetamide, and the like or mixtures thereof. Each possibility represents a separate embodiment of the invention. Suitable anti-foaming agents include, but are not limited to, silicon emulsions or sorbitan sesquioleate. Suitable stabilizers to prevent or reduce the deterioration of the components in the compositions of the present invention include, but are not limited to, antioxidants such as glycine, a-tocopherol or ascorbate, BHA, BHT, and the like or mixtures thereof. Each possibility represents a separate embodiment of the invention. Suitable tonicity modifiers include, but are not limited to, mannitol, sodium chloride, and glucose. Each possibility represents a separate embodiment of the invention. Suitable buffering agents include, but are not limited to, acetates, phosphates, and citrates with suitable cations. Each possibility represents a separate embodiment of the invention.

The particle size of the "water-in oil-in water (w/o/w) double emulsion" can be determined by various parameters including, but not limited to, the amount of applied force at this step, the speed of mixing, surfactant type and concentration, etc. Suitable particle sizes range from about 1 to 100 µm.

The depot systems of the present invention encompass any forms known to a person of skill in the art. Suitable forms include, but are not limited to, biodegradable or non-biodegradable microspheres, implantable rods, implantable capsules, and implantable rings. Each possibility represents a separate embodiment of the invention. Further contemplated are prolonged release gel depot and erodible matrices. Each possibility represents a separate embodiment of the invention. Suitable implantable systems are described for example in US 2008/0063687, the content of which is hereby incorporated in its entirety. Implantable rods can be prepared as is known in the art using suitable microextruders.

In some embodiments, the depot formulations of the present invention include, but are not limited to, suspensions of glatiramer acetate in water, oil or wax phase; poorly soluble polyelectrolyte complexes of glatiramer acetate; "in-situ" gel-forming matrices based on the combination of water-miscible solvent with glatiramer acetate; and biodegradable polymeric microparticles with incorporated glatiramer acetate. Each possibility represents a separate embodiment of the invention. In particular, the compositions of the present invention are in the form of injectable microparticles wherein the glatiramer acetate is entrapped in a biodegradable or non-biodegradable carrier. The microparticulate compositions of the present invention may comprise a water-in oil-in water double emulsion. Within the scope of the present invention is a microparticulate composition comprising an internal aqueous phase comprising glatiramer or any pharmaceutically acceptable salt thereof, an oil phase or water-immiscible phase comprising a biodegradable or non-biodegradable polymer and an external aqueous phase. The external aqueous phase may further comprise a surfactant, preferably polyvinyl alcohol (PVA), polysorbate, polyethylene oxide-polypropylene oxide block copolymers or cellulose esters. The terms "oil phase" and "water-immiscible phase" may be used interchangeably herein.

According to some embodiments, the glatiramer acetate comprises the acetate salt of L-alanine, L-glutamic acid, L-lysine, and L-tyrosine in the molar ratios of about 0.14 glutamic acid, about 0.43 alanine, about 0.10 tyrosine and about 0.33 lysine. According to other embodiments, the glatiramer acetate or other pharmaceutically acceptable salt of glatiramer comprises about 15 to about 100 amino acids.

In certain embodiments, the depot formulation is self-administered intramuscularly by the patient. In certain embodiments, the depot formulation is injected into the deltoid muscle.

Encompassed by the present invention is a combination therapy of glatiramer acetate or any other pharmaceutically acceptable salt of glatiramer with at least one other active agent. Active agents within the scope of the present invention include, but are not limited to interferons, e.g. pegylated or non-pegylated α-interferons, or β-interferons, e.g. interferon β-1a or interferon β-1b, or τ-interferons; immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH; adenosine deaminase inhibitors, e.g. cladribine; IV immunoglobulin G (e.g. as disclosed in Neurology, 1998, May 50(5): 1273-81) monoclonal antibodies to various T-cell surface markers, e.g. natalizumab (ANTEGREN®) or alemtuzumab; TH2 promoting cytokines, e.g. IL-4, IL-10, or compounds which inhibit expression of TH1 promoting cytokines, e.g. phosphodiesterase inhibitors, e.g. pentoxifylline; antispasticity agents including baclofen, diazepam, piracetam, dantrolene, lamotrigine, rifluzole, tizanidine, clonidine, beta blockers, cyproheptadine, orphenadrine or cannabinoids; AMPA glutamate receptor antagonists, e.g. 2,3-dihydroxy-6-nitro-7-sulfamoylbenzo(f)quinoxaline, [1,2,3,4,-tetrahydro-7-morpholin-yl-2,3-dioxo-6-(trifluoromethyl)quinoxalin-i-yl]methylphosphonate, 1-(4-aminophenyl)-4-methyl-7,8-methylene-dioxy-5H-2,3-benzodiazepine, or (−)1-(4-aminophenyl)-4-methyl-7,8-methylene-dioxy-4,5-dihydro-3-methylcarbarnoyl-2,3-benzodiazepine; inhibitors of VCAM-1 expression or antagonists of its ligand, e.g. antagonists of the α4β1 integrin VLA-4 and/or α-4-β-7 integrins, e.g. natalizumab (ANTEGREN®); anti-macrophage migration inhibitory factor (Anti-MIF); xii) Cathepsin S inhibitors; xiii) mTor inhibitors. Each possibility represents a separate embodiment of the invention. Currently preferred one other active agent is FTY720 (2-amino-2-[2-(4-octylphenyl)ethyl] propane-1,3-diol; fingolimod) belonging to the class of immuno-suppressants. Another possibility is to combine glatiramer acetate with treatment by ocrelizumab (OCREVUS™), a humanized anti-CD20 monoclonal antibody, which is the only therapy currently approved for treatment of PPMS.

In more specific embodiments, the sustained release depot formulation comprises a therapeutically effective amount of a pharmaceutically acceptable salt of glatiramer, the formulation being in a sustained release depot form which releases a therapeutically effective amount of the pharmaceutically acceptable salt of glatiramer over a period of about one week to about 6 months. In certain embodiments, the sustained release depot formulation comprises a therapeutically effective amount of a pharmaceutically acceptable salt of glatiramer in depot form suitable for implantation at a medically acceptable location in a subject in need thereof. In certain embodiments, the glatiramer comprises L-alanine, L-glutamic acid, L-lysine, and L-tyrosine in molar ratios of about 0.14 glutamic acid, about 0.43 alanine, about 0.10 tyrosine and about 0.33 lysine. In certain embodiments, the glatiramer comprises about 15 to about 100 amino acids. In certain embodiments, the sustained release depot formulation further comprises a pharmaceutically acceptable biodegradable or non-biodegradable carrier. In certain embodiments, the carrier is selected from poly (D,L-lactide-co-glycolide) (PLGA), poly (D,L-lactide) (PLA), polyglycolides (PGA), polycaprolactone, polyhydroxybutyrate, polyorthoesters, polyalkaneanhydrides, gelatin, collagen, oxidized cellulose, and polyphosphazene. In certain embodiments, the sustained release depot formulation is in the form of microparticles prepared by a water-in oil-in water double emulsification process. In certain embodiments, the sustained release depot formulation comprises an internal aqueous phase comprising a therapeutically effective amount of a pharmaceutically acceptable salt of glatiramer, a water immiscible polymeric phase comprising a biodegradable or non-biodegradable polymer and an external aqueous phase. In certain embodiments, the water immiscible polymeric phase comprises a biodegradable polymer selected from poly (D,L-lactide) (PLA) and poly (D,L-lactide-co-glycolide) (PLGA). In certain embodiments, the external water phase comprises a surfactant selected form polyvinyl alcohol (PVA), polysorbate, polyethylene oxide-polypropylene oxide block copolymers and cellulose esters. In certain embodiments, the sustained release depot formulation is in the form of biodegradable microspheres, non-biodegradable microspheres, implants of any suitable geometric shape, implantable rods, implantable capsules, implantable rings, or prolonged release gels or erodible matrices. In certain embodiments, the sustained release depot formulation provides equal or superior therapeutic efficacy to the commercially available daily or thrice weekly injectable dosage forms of glatiramer acetate, with reduced incidence of side effects and/or with reduced severity of side effects at the local and/or systemic level. In certain embodiments, the sustained release depot formulation provides prolonged release or prolonged action of glatiramer in a subject as compared to a substantially similar dose of an immediate release formulation of glatiramer acetate.

In certain embodiments, the sustained release depot formulation further comprises at least one additional drug. In certain embodiments, the at least one additional drug is an immunosuppressant. In certain embodiments, the at least one additional drug is fingolimod. In certain embodiments, the sustained release depot formulation comprises the pharmaceutically acceptable salt of glatiramer in a dose ranging from about 20 to about 750 mg. In certain embodiments, the pharmaceutically acceptable salt of glatiramer is selected from the group consisting of sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, tocopheryl succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, .beta.-hydroxybutyrate, glycollate, tartrate, methanesulfonate, propanesulfonate, naphthalene-2-sulfonate, p-toluenesulfonate, and mandelate. Each possibility represents a separate embodiment of the present invention. In certain embodiments, the therapeutically acceptable amount of said pharmaceutically acceptable salt of glatiramer is about 1 to about 500 mg/day, or about 20 mg to about 200 mg/day.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1: In-Vitro Preparation Method of 40 mg GA in PLGA Depot

Preparation Process: (1) External water phase preparation: Partially hydrolyzed polyvinyl alcohol (PVA) solution at a concentration of 2% w/w in sterile WFI was prepared in a reactor and filtered through a 0.22 µm membrane. (2) A solution of NaCl in sterile WFI was prepared and filtered through a 0.22 µm membrane into the reactor containing the PVA. (3) Organic phase preparation: Organic phase composed of dichloromethane and poly(lactide-co-glycolide) was prepared in a reactor and filtered through a 0.22 µm membrane. (4) Internal water phase preparation: A solution containing sterile WFI and glatiramer acetate was prepared and filtered through a 0.22 µm membrane. (5) Water-in-oil (w/o) emulsion preparation: Internal water phase was added to the organic phase and processed using IKA Ultra-Turrax T50 homogenizer equipped with a rotor stator dispersion device at 7,200 RPM for 10 minutes (high shear mixing). (6) Water-in-oil-in-water (w/o/w) emulsion preparation: Water in oil emulsion (w/o) prepared in step 5 was added to half of the external water phase during continuing mixing of the w/o emulsion. The w/o/w double emulsion was processed using IKA Ultra-Turrax UTS80 homogenizer with a rotor stator head at 2,900 RPM for 3 minutes from the end of w/o transfer into the external water phase. Following, another 30 liters of the external water phase was added to the emulsion (quench). (7) Solvent removal/evaporation: The w/o/w double emulsion formed in step (6) was mixed using the IKA UTS80 homogenizer at different speeds for 15-17 hours. Compressed air was bubbled at 0.5 Pa through the emulsion for 10-12 hours. Vacuum was applied for the portion of the process. (8) Separation and washing: The suspension was centrifuged at 5,300 RPM for 10 minutes. The supernatant was discarded and the pellet (sediment microparticles) is resuspended in 550 g WFI and mixed using a magnetic stirrer for 3 minutes. The resuspended microparticles were centrifuged at 2900 RPM for 10 minutes. (9) Lyophilization: The washed microparticles were resuspended in about 750 g sterile WFI and are kept at −20° C. until lyophilization. Lyophilization was carried out using sterile lyoguard trays as follows: Freeze at −40° C., 24 hours. Primary drying at 0.2 hPa, −5° C., 48 hours. Secondary drying at 0.2 hPa, 10° C., 48 hours. The resulting composition includes GA and PLGA (50:50, molecular weight 7,000-17,000) in a 1:11.5 weight ratio.

Example 2: In-Vitro Release Profile of 40 mg GA from a PLGA Depot

The release of the incorporated glatiramer acetate was carried out in tightly closed 20 ml glass vials, using incubator at 37° C., equipped with a multi-point magnetic stirrer. Phosphate buffered saline (PBS) with pH 7.4 was used as a release media. Table 1 summarizes the release profile of GA from a PLGA Depot.

TABLE 1

| | Days | | | | | | | | |
|---|---|---|---|---|---|---|---|---|---|
| | 0 | 1 | 5 | 8 | 13 | 15 | 22 | 27 | 32 |
| % GA released into medium | 14 | 15 | 21 | 25 | 34 | 43 | 80 | 96 | 99 |

Example 3: Depot of 40 mg GA Vs. Commercially Available GA (Copaxone®) In-Vivo Material and Methods Animals: All animal studies were approved by the Israeli MOH Animal Care and Use Committee. C57BL/6 female mice, 7-9 weeks old were randomized into control or treatment groups with similar mean weight. Animals were given food and water ad-libitum throughout the experiment.

Induction of progressive EAE: In order to induce primary progressive EAE (PP-EAE) which most resembles progressive forms of MS in humans (Sayed et al., The Journal of Immunology, 2011, Vol. 186, 3294-3298), an emulsion of MOG 35-55 (GL Biochem co. Ltd, Shanghai, China) in Modified Complete Freund's adjuvant (CFA) (Sigma-Aldrich, St. Louis, MO, USA) was prepared as follows: heat-killed *M. tuberculosis* Strain H37RA (Sigma) was added to CFA to a final concentration of 4 mg/mL. Subsequently, 2 mg/mL MOG 35-55 were emulsified with equal amount of modified CFA. EAE had been induced by injection of this emulsion subcutaneously (SC) on the shaved back of the mouse at one site, followed by an intraperitoneal injection of *Bordetella pertussis* toxin (Sigma) in PBS on Day 0 and 48 hours post MOG immunization. A 21G needle was used for injections in mice. This model displays a robust inflammation stage on days 9 to 15 in which demyelinization as well as axonal damage is evident. Following this stage, inflammation is usually very moderate.

Measurements: Body weight was measured every two days from day 0 to day 28. EAE was assessed by clinical scoring of the mice once daily from Day 0 to Day 28 post immunization (Table 2). For analysis, dead animals received clinical score of 5 and the weight recorded at the last measurement before animal death.

TABLE 2

EAE clinical Score in Mice.

| Score | Clinical signs |
|---|---|
| 0 | Normal mouse; no overt signs of disease |
| 1 | Limp tail |
| 2 | Hind limb paralysis |
| 3 | Hind and front limb paralysis |
| 4 | Complete paralysis: sacrifice for humane reasons |
| 5 | Moribund state; Death by EAE |

The following calculations were derived from clinical score raw data: mean maximum score is the mean of the highest scores noted for each mouse in a specific group up to indicated day of analysis; mean disease duration and mean day of onset were calculated as follows: Mean Disease Duration=Sum of (day of analysis−day of disease onset for each mouse)/(number of mice per group); Mean Day of Onset=(sum of day of disease onset of each mouse)/(number of mice per group). Area under the curve (AUC) of clinical score was calculated using Microsoft Excel and represents disease burden.

Glatiramer Acetate Depot (GA Depot): GA Depot was suspended in water for injection (WFI) and immediately injected intramuscularly (IM) at the indicated dose. Dose of GA Depot are given according to amount of active ingredient (i.e. GA Depot 4 mg contains 4 mg GA).

GA Binding Antibodies Analysis: At day 35 following disease induction, 5 animals from each treatment group were sacrificed. Blood samples were retrieved and serum was isolated and stored at −80° C. (see Tables 3 and 5).

ELISA plates were prepared as following: flat bottom ELISA plates (Nunc) were coated with 100 μl of 50 μg/ml GA in borate buffer (BB) 0.17 M pH 8.0 overnight at 4° C. Wells were emptied and washed with phosphate buffer saline (PBS) containing 0.05% Tween 20 at room temperature. Following the washing 1% BSA was applied for 2 hours at room temperature (RT), for blocking of non-specific binding sites. Subsequently, wells were washed three times with wash solution.

ELISA test was performed as follows: 100 μl of sera samples were diluted 1:1,000 added to wells for 18 hours at 4° C. (sera dilution was performed using PBS containing 1% BSA and 0.05% Tween 20), followed by three washes with phosphate buffer saline (PBS) containing 0.05% Tween 20 at room temperature. Subsequently, 100 μl 1:50,000 diluted alkaline phosphatase conjugated AffinityPure Goat anti-mouse IgG+IgM (H+L) (Jackson Laboratories) was added to the wells and incubated for 2 hours at RT. The wells were washed again three times using wash solution and the color reaction was developed by adding 100 μl of the substrate p-nitrophenyl phosphate (Jackson Laboratories) and incubation for 40-60 min at RT. The reaction was terminated with 30 μl 3N NaOH. The absorbance at 405 nm was then recorded using micro-ELISA reader (Dynatech). Each assay plate contained positive anti-GA serum samples and control of normal mouse serum (N=5).

The results were expressed as Binding Index (BI) according to the following formula: Binding Index=mean optical density of tested serum/mean optical density of control serum. The mean value for normal mice serum was 0.230 OD and the cut off values for Binding Index is 2.0±1.0. Thus, values above 3.0 were considered as positive.

Experimental Design: Studies experimental design is specified in Table 3.

TABLE 3

Experimental design.

| Group | Test Article, N = 20/Group | Route | Dose | Days of Administration | Solvent |
|---|---|---|---|---|---|
| 1 | GA Depot | IM | 4 mg | 0, 1* | WFI, 0.2 mL |
| 2 | Copaxone ® | SC | 2 mg | 0-8, 9 in total | N/A |
| 3 | Untreated Control (saline) | SC | N/A | 0-8, 9 in total | Saline, 0.1 ml |

*Dose was administered using two injections on consecutive days since there is a maximal volume of injection that can be tolerated in a single injection in mice.

Statistical analysis: Data was analyzed using Microsoft Excel. Each data set was analyzed using single-factor analysis of variance (ANOVA) followed by one tailed student's T-test.

GA Depot Dose Conversion

FIG. 1 shows mean clinical score results for saline control (black sphere marker), 2 mg Copaxone® (black square marker) and GA Depot 4 mg (gray triangle marker) groups, as those groups represent the range of the proposed human dose (using an allometric 1:10 scale, as deducted from previous studies) of 0, 20 and 40 mg, respectively. *P<0.05 for all treatment groups compared with untreated control, Single Factor ANOVA followed by one-tailed T Test assuming unequal variance. N=20/group, +/−standard error.

Figure 2:
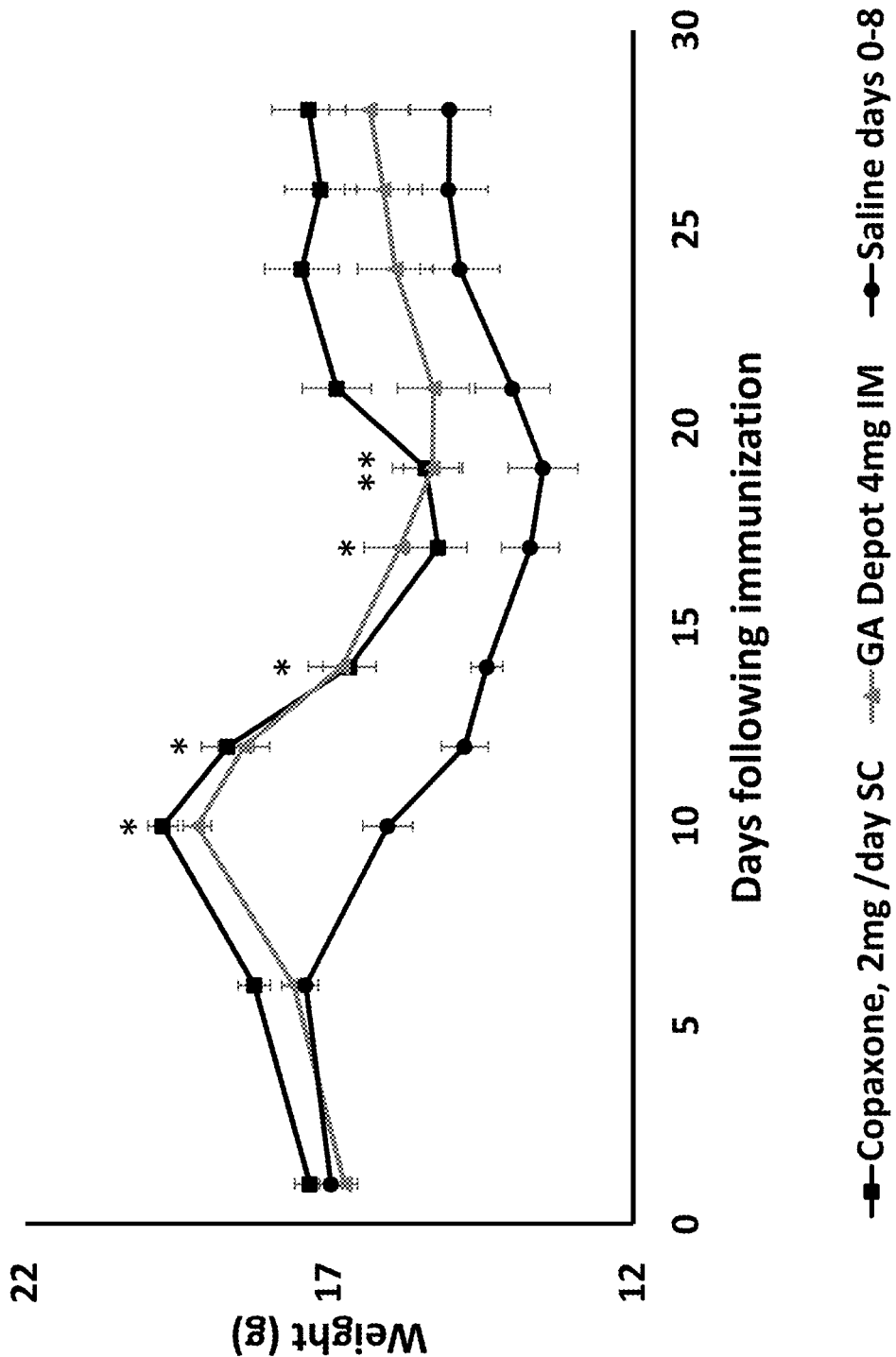
FIG. 2 illustrates the mean body weight results for saline control, Copaxone® (2 mg GA, days 0-8) and GA Depot (4 mg GA, day 0) in C57BL/6 mice groups. *P<0.05 for all treatment groups compared with untreated control, Single Factor ANOVA followed by one-tailed T Test assuming unequal variance. N=20/group, +/−standard error.

Mean clinical score AUC (area under curve), mean day of onset and mean disease duration were significantly reduced in the GA Depot group and in the Copaxone® group compared with untreated control (Table 4, p<0.05). No statistically significant difference was found between the GA Depot and Copaxone® at any of the computed values (Table 4). At days 11-19, mean clinical score of the saline group was significantly higher than that of all other groups (FIG. 1, p<0.05). At day 20, mean clinical score of the saline group was significantly higher than that of Copaxone® and the GA Depot groups (FIG. 1, p<0.05). Body weight of the GA Depot and Copaxone® treated groups was significantly higher than that of the untreated control at days 10 to 17 following immunization. At day 21, body weight of the Copaxone® group was significantly higher than that of the untreated control group (FIG. 2, P<0.05). *P<0.05 for all treatment groups compared with untreated control. ** P<0.05 for Copaxone® group compared with untreated control. Single Factor ANOVA followed by one-tailed T Test assuming unequal variance. N=20/group, +/−standard error.

TABLE 4

Calculated Values.

| Groups | Maximum Mean Disease Score | Mean Disease Duration* | Mean Day of Onset* | AUC Clinical Score* | Survival Rate at Day 28 |
|---|---|---|---|---|---|
| GA Depot 4 mg IM Day 0, 1 | 2.55 ± 0.25 | 15.05 ± 0.51 | 12.95 ± 0.51 | 29.85 ± 2.59 | 85% |
| Copaxone ® 2 mg SC, Days 0-8 | 2.25 ± 0.22 | 15.65 ± 0.23 | 12.35 ± 0.23 | 26.83 ± 2.49 | 90% |
| Control (saline, SC) D0-D8 | 3.15 ± 0.24 | 17.80 ± 0.09 | 10.20 ± 0.09 | 42.89 ± 3.22 | 80% |

*P < 0.05 for all treatment groups compared with untreated control, Single Factor ANOVA followed by one-tailed T Test assuming unequal variance.
N = 20/group, +/−standard error.

Immunological Response in Mice Measured by Antibodies to GA

Serum was isolated from mice in MOG-EAE study at day 35 following disease induction. Mice were treated with either the GA Depot (at 4 mg once) or Copaxone® (2 mg/day, days 0-8). Antibodies (Abs) titer was evaluated using an ELISA assay. Results are expressed as Binding Index (BI). N=5. Data as presented in Table 5 demonstrate that mice exposed to Copaxone® or to the GA Depot developed similar titer of total anti-GA antibodies while control mice that were treated with saline had no such antibodies. The antibodies titer was similar in all treatment groups, suggesting a similar immunological response.

TABLE 5

Binding Index.

| | Saline control | GA Depot 4 mg | Copaxone ® 2 mg |
|---|---|---|---|
| Binding Index | 1.71 | 9.48 | 11.14 |

The data presented, comparing the effect of a single administration of the 4 mg GA Depot across to the standard daily administration of 2 mg GA, show similar efficacy between the two dosage regimes. Specifically, the GA Depot showed a clear significant effect of delayed disease onset and amelioration of symptoms, at least as effective as noted for the Copaxone® treated group (see FIG. 1).

In addition, this experiment shows that intramuscular administration of the GA Depot induced a humoral response of anti-GA antibodies, at similar levels as with standard daily subcutaneous injection of GA (see Table 5). Therefore, the similar humoral responses to GA Depot as compared to standard GA injections might represent a similarity in the immunologic response to the GA Depot. This may therefore indicate also equivalent clinical immuno-modulatory therapeutic effects, as can be seen in this EAE study of which the AUC between Copaxone® and GA Depot are not different in statistical significant manner (see Table 4). Therefore, the existence of anti-GA antibodies can serve as a biomarker to the therapeutic bio-availability of the drug, when with a new formulation and administered via a new route.

Overall, data supports that the efficacy of GA Depots at dose of 4 mg GA in MOG-induced EAE is at least comparable to that of Copaxone® and that the immune response to both treatments is similar.

Example 4: Depots of 40 mg or 80 mg GA in Humans Diagnosed with PPMS

Brief Summary: A prospective, multicenter, single arm, open label, phase IIa study to assess the safety and efficacy of once-a-month long-acting intramuscular injection of 40 mg Glatiramer Acetate (GA Depot) in subjects with Primary Progressive Multiple Sclerosis (PPMS).
Primary endpoints: Safety and tolerability: Assessments of adverse events (AEs); Assessments of injection sites reactions (ISRs).
Secondary endpoints: Efficacy: Time to onset of 12 weeks Confirmed Disease Progression (CDP) assessed by EDSS; Defined as an increase of ≥1 point from baseline EDSS score that was sustained on subsequent visits for at least 12 weeks. MRI assessments: Percent of whole brain volume change; Percent of cortical volume change.
Exploratory endpoints: Efficacy analysis: Change from baseline in Timed 25-foot walk (T25FW). Change from baseline in 9-HPT assessment. MRI assessments: New and enlarging T2 lesions; T2-lesion volume; New and enlarging T1 lesions; T1-lesion volume; Gadolinium (Gd)-lesion number; Gadolinium (Gd)-lesion volume.
Procedures: Subjects visit the site every 4 weeks to receive the GA Depot (40 mg) IM injection administered by a Health care professional (HCP); and are evaluated by the investigator at screening, baseline, 1 week after the second GA Depot injection, 3 months after the first injection and every 3 months thereafter until end of treatment period. A follow up (FU) visit to assess patients' safety is scheduled one month after EoT.
Evaluation criteria: LP: CSF test: Performed at screening visit (IgG OCB) unless the subject has a CSF test prior to screening visit. MRI scans: Performed at screening, week 24 and week 52 (EoT visit). Neurological evaluations, including EDSS, T25FW & 9-HPT performed at screening, baseline, 3 months, and then every 3 months until end of treatment. Adverse events (AEs): monitored throughout the study period. Vital signs: blood pressure (BP) and heart rate recorded at each visit. BP (systolic and diastolic) measured twice at each visit (each measurement separated by a few minutes). Physical examination: A full physical examination performed to ensure suitability per the inclusion and exclusion criteria at screening, baseline, 1 week after the second GA Depot treatment, 3 months after first GA Depot treatment and every 3 months thereafter. Last physical examination performed at FU visit. Clinical laboratory testing: Laboratory tests for chemistry, hematology and urinalysis taken at screening, baseline, 1 month after first treatment, 3, 6, 9 months and at EoT visit. Hematology test include: hemoglobin, red cell count, MCV, hematocrit, MCH, white cell count, differential white cell count, platelet count.

Chemistry test include: creatinine, glucose, blood urea nitrogen (BUN), alkaline phosphatase, alanine aminotransferase (ALT/SGPT), aspartate aminotransferase (AST/SGOT), gamma glutamyl transpeptidase (GGT), total bilirubin, protein, albumin, albumin/globulin ratio, sodium, potassium, chloride, calcium, uric acid, CPK, cholesterol, triglycerides. Urinalysis—stick test performed at site.

Each patient is compared to his individual baseline test taken at screening visit. When in the subject's best interest, additional tests may be performed at the discretion of the Investigator to ensure their good health.

Antibodies testing: Blood samples for total Glatiramer Acetate IgG binding antibodies and detection of neutralizing antibodies to Glatiramer Acetate taken at baseline, 1 month after the first GA Depot injection, 3 months, and every 3 months thereafter. 12-lead ECG performed at screening. The ECG is recorded while the subject is resting in supine position. 6 limb leads, as specified by Einthoven (I, II and III) and Goldberger (aVR, aVL, aVF), and 6 pre-cordial leads (V1-V6), according to Wilson, are used. The investigator assesses the parameters HR, RR, PQ, QRS, QT and QTc. Additionally, the occurrence of de- or repolarization disorders, arrhythmic disorders or other abnormalities is assessed and recorded. Chest x-ray performed at screening if not performed within 6 months prior to screening visit.

Treatment location and patient supervision: Study injections are administered and monitored at site. Subjects stay at the study site for observation for 1 hour following the first GA Depot injection and half an hour following the subsequent GA Depot injections to ensure their well-being.

Trial treatments, dosage, and dosage regimen of the investigational products: All enrolled subjects are treated with GA Depot (40 mg) IM at 4 week intervals for a total of 52 weeks of treatment.

Expected duration of subject participation, sequence, and duration of all trial periods including follow-up: The study duration for an individual subject is up to 14 months, consisting of the screening period and 12 months of treatment followed by a follow up visit as follows: up to 4 weeks of screening period (weeks −4 to 0), 52 weeks of open-label treatment period, an EoT visit at week 52 and a follow-up visit 4 weeks after the EoT visit.

Subject inclusion criteria: Subjects must fulfill all the following criteria before being included in the study: Male or female subjects diagnosed with PPMS. Diagnosis of PPMS consistent with the McDonald Criteria (revisions of 2010); Age between 18 and 60 years (inclusive); Subjects diagnosed with PPMS for at least 1 year and a sustained increment of ≥1 point in the EDSS score in the last year prior to screening; EDSS≥2 and ≤5.5 (Pyramidal or Cerebellar FS≥2); Documented history or the presence at screening of >1 oligoclonal band (OCB) if quantitative testing was done, or OCB+ if no quantitative testing was done, and/or positive IgG index in the cerebrospinal fluid (CSF); Subjects with at least 1 gadolinium-enhancing lesion on baseline MRI and/or documented in previous MRI within 12 months prior to screening visit; Women of child bearing potential must have a negative urine pregnancy test at screening and use an adequate contraceptive method throughout the study; Ability to provide written informed consent.

Subject exclusion criteria: Subjects are to be excluded from the study if they display any of the following criteria: RRMS, SPMS, or PRMS; Documented history of relapse events; Any relevant medical, surgical, or psychiatric condition, laboratory value, or concomitant medication which, in the opinion of the investigator, makes the subject unsuitable for study entry or potentially unable to complete all aspects of the study; Contraindications or inability to successfully undergo magnetic resonance imaging (MRI) scanning; Subjects diagnosed with any systemic autoimmune disease other than MS that may impact the CNS with MS like lesions such as Sarcoidosis, Sjögren's syndrome, Systemic Lupus Erythematosus (SLE), Lyme disease, APLA syndrome, etc. Subjects with stable local/organ autoimmune disease such as psoriasis, Cutaneous Lupus erythematosus, thyroiditis (Hashimoto, grave) etc. may be considered eligible upon the PI's discretion; Severe anemia (hemoglobin<10 g/dL); Abnormal renal function (serum creatinine>1.5×ULN or creatinine clearance<30 ml/min); Abnormal liver function (transaminases>2×ULN); Pregnant or breast-feeding women; Treatment with any kind of steroids during the last month prior to screening visit; History of any anaphylactic reaction and/or serious allergic reaction following a vaccination, a known hypersensitivity to any component of the study drug, e.g. glatiramer acetate (GA), polylactic-co-glycolic acid (PLGA), polyvinyl alcohol (PVA); Known or suspected history of drug or alcohol abuse; Known as positive for HIV, hepatitis, VDRL, or tuberculosis; Active malignant disease of any kind. However, a patient, who had a malignant disease in the past, was treated and is currently disease—free for at least 7 years, may be considered eligible, upon the PI and sponsor discretion; Previous treatment with B-cell-targeting therapies (e.g. rituximab, ocrelizumab, atacicept, belimumab or ofatumumab) 6 months prior to screening; Previous treatment with cladribine within 2 years prior to screening visit; Previous treatment with azathioprine, mitoxantrone or methotrexate within 6 months prior to screening visit; Previous treatment with lymphocyte-trafficking modifiers (e.g. natalizumab, fingolimod) within 6 months prior to screening visit. Subjects should have a total lymphocyte count within normal range; Previous treatment with beta interferons, intravenous immunoglobulin, plasmapheresis within 2 months prior to screening visit; Previous treatment with any glatiramer acetate therapy within 3 months prior to screening visit; Uncontrolled diabetes; Participation in an investigational study drug within 30 days prior to study entry.

Formulation and dosing of study drug: GA Depot is a combination of extended-release microspheres containing GA for injection and diluent for parenteral use. The extended-release microsphere formulation is a white to off-white, free-flowing powder in dosage strength of 40 mg GA per vial. GA is micro-encapsulated in poly (D,L-lactide-co-glycolide) (50:50) acid terminated, at a concentration of 80 mg GA per gram of microspheres plus 10% overage to compensate for withdrawal losses. The diluent for parenteral use is water for injection. The microspheres are suspended in the diluent prior to injection.

Test treatment: IP: long-acting Glatiramer Acetate (GA Depot). Formulation: 550 mg of lyophilized PLGA-encapsulated glatiramer acetate containing 40 mg GA. Water for injection (WFI): 10 ml ampule. 1.6 ml WFI are used for suspension of one 40 mg GA Depot vial to reach a final 2 ml volume of suspension for injection. Route of administration: Intramuscular. Unit dose: 40 or 80 mg GA Depot. Dosage schedule: Each subject receives 40 or 80 mg of GA Depot administered IM once every 4 weeks, 13 times for a total of 52 weeks of treatment.

Specification of efficacy/pharmacology parameters: The following clinical and efficacy parameters are assessed: EDSS score; MRI assessments (whole brain volume, cortical brain volume, new and enlarging T2 lesions, T2-lesion volume, new and enlarging T1 lesions, T1-lesion volume, Gadolinium (Gd)-lesion number, Gadolinium (Gd)-lesion volume); Timed 25-foot walk (T25FW); and/or 9-HPT.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method of suppressing or alleviating a symptom or a plurality of symptoms of primary progressive multiple sclerosis (PPMS) or secondary progressive multiple sclerosis (SPMS) in a patient diagnosed with primary progressive multiple sclerosis (PPMS) or secondary progressive multiple sclerosis (SPMS), the method comprising administering or implanting a sustained release depot formulation comprising a 40 mg to 80 mg dose of glatiramer acetate to the patient, wherein the patient has been diagnosed with PPMS for at least 1 year and with signs of disease progression in the year prior to treatment, with a sustained increment in a rate of >1-point increase per year in the EDSS Expanded Disability Status Scale) score and has an EDSS score of between 2-5.5 or with a sustained increment in a rate of >0.5 point increase per year in the EDSS score and has an EDSS score of >5; and wherein suppressing or alleviating a symptom or a plurality of symptoms of PPMS or SPMS comprises increasing the time to onset of 12 week Confirmed Disease Progression (CDP) of the patient assessed by the EDSS, compared to a baseline of the EDSS from the patient before the treatment or the EDSS from the untreated control patient.

2. The method of claim 1, wherein the patient:
(i) has a documented history of, or the presence of more than 1 oligoclonal band (OCB) if quantitative testing was done, or OCB+ if no quantitative testing was done, and/or positive IgG index in the cerebrospinal fluid (CSF);
(ii) has at least 1 gadolinium-enhancing lesion on MRI and/or at least 1 gadolinium-enhancing lesion documented within the previous year on MRI; or
(iii) any combination of (i) to (ii).

3. The method of claim 1, wherein the method further comprises suppressing or alleviating at least one symptom selected from the group consisting of impaired walking capability, weakness of the leg, stiffness of the leg, impaired balance, impaired coordination, impaired memory, impaired cognitive function, a difficulty to swallow, impaired vision, general fatigue, pain, impaired bladder function, impaired bowel function, and any combination thereof.

4. The method of claim 1, wherein the method further comprises:
(i) decreasing whole brain volume change or cortical volume change of the patient, compared to baseline or untreated control;
(ii) decreasing time needed for the patient to complete a timed 25-foot walk (T25FW) test, compared to baseline or untreated control;
(iii) decreasing time needed for the patient to complete a 9-Hole Peg Test (9-HPT), compared to baseline or untreated control;
(iv) decreasing number of new or enlarging T2 lesions in the brain of the patient, compared to baseline or untreated control;
(v) decreasing volume of T2 lesions in the brain of the patient, compared to baseline or untreated control;

(vi) decreasing number of new or enlarging T1 lesions in the brain of the patient, compared to baseline or untreated control;

(vii) decreasing volume of T1 lesions in the brain of the patient, compared to baseline or untreated control;

(viii) decreasing number or volume of Gadolinium (Gd) lesions in the brain of the patient, compared to baseline or untreated control;

(ix) reducing rate of progression of PPMS or SPMS, compared to baseline or untreated control; or (x) any combination of (i) to (ix).

5. The method of claim 1, wherein the patient is diagnosed with primary progressive multiple sclerosis (PPMS).

6. The method of claim 1, wherein the patient has an EDSS score of <5.5 and CDP is at least a 1 point increase of the EDSS score.

7. The method of claim 1, wherein the baseline is a period of 12 weeks or more prior to treatment by the depot formulation.

8. The method of claim 1, wherein the depot formulation is administered or implanted intramuscularly.

9. The method of claim 1, wherein the depot formulation comprises a 40 mg dose of glatiramer acetate.

10. The method of claim 1, wherein the depot formulation is administered in a therapeutically effective regime of once every 1 to 15 weeks.

11. The method of claim 10, wherein the depot formulation is administered once every 4 weeks.

12. The method of claim 10, wherein the depot formulation is repeatedly administered during 1 year or more.

13. The method of claim 1, wherein the depot formulation comprises 20% to 30% solids.

14. The method of claim 1, wherein the depot formulation comprises a Poly(Lactide-co-Glycolide) (PLGA) copolymer.

15. The method of claim 14, wherein the depot formulation comprises 550 mg PLGA copolymer per 40 mg of glatiramer acetate.

16. The method of claim 14, wherein the PLGA copolymer at least partly encapsulates the glatiramer acetate.

17. The method of claim 1, wherein the depot formulation, in phosphate buffered saline (PBS, pH 7.4), in a closed vial, at 37° C., while stirring:

(i) releases about 15% to about 30% of the glatiramer acetate within 1 week;

(ii) releases about 30% to about 50% of the glatiramer acetate within 2 weeks;

(iii) releases about 50% to about 90% of the glatiramer acetate within 3 weeks;

(iv) releases about 90% to about 100% of the glatiramer acetate within 4 weeks; or (v) any combination of (i) to (iv).

* * * * *